United States Patent
Cihlar et al.

(10) Patent No.: US 10,059,697 B2
(45) Date of Patent: Aug. 28, 2018

(54) COMPOUNDS AND COMBINATIONS FOR THE TREATMENT OF HIV

(71) Applicant: Gilead Sciences, Inc., Foster City, CA (US)

(72) Inventors: Tomas Cihlar, Foster City, CA (US); Michael Graupe, Pacifica, CA (US); Yunfeng Eric Hu, San Mateo, CA (US); Jeffrey Patrick Murry, Castro Valley, CA (US); Derek Dean Sloan, Belmont, CA (US); George Stepan, Union City, CA (US); Helen Yu, Mountain View, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/280,801

(22) Filed: Sep. 29, 2016

(65) Prior Publication Data

US 2017/0114048 A1    Apr. 27, 2017

Related U.S. Application Data

(60) Provisional application No. 62/235,302, filed on Sep. 30, 2015.

(51) Int. Cl.
| | | |
|---|---|---|
| *C07D 405/12* | (2006.01) | |
| *A61K 31/4196* | (2006.01) | |
| *A61K 31/69* | (2006.01) | |
| *A61K 38/06* | (2006.01) | |
| *A61K 38/07* | (2006.01) | |
| *A61K 45/06* | (2006.01) | |

(52) U.S. Cl.
CPC ........ *C07D 405/12* (2013.01); *A61K 31/4196* (2013.01); *A61K 31/69* (2013.01); *A61K 38/06* (2013.01); *A61K 38/07* (2013.01); *A61K 45/06* (2013.01)

(58) Field of Classification Search
None
See application file for complete search history.

(56) References Cited

U.S. PATENT DOCUMENTS

2015/0216926 A1    8/2015   Kutsch et al.

FOREIGN PATENT DOCUMENTS

| WO | WO-1994/05276 | 3/1994 |
| WO | WO-2007/134037 | 11/2007 |
| WO | WO-2010/108187 | 9/2010 |

OTHER PUBLICATIONS

Ito et al. In Cancer Science 94(1), 3-8 (2003).*
STN Registry Database entry for CAS RN 1008352-54-2, Entry date Mar. 16, 2008, Accessed Apr. 5, 2017.*
Xing et al., Drug Discovery Today, vol. 18, Issues 11-12, Jun. 2013, pp. 541-551.*
Jay A. Levy, New England Journal of Medicine, 360; 7, pp. 724-725 (2009).*
Archin et al. 2014 "Eradicating HIV-1 Infection: Seeking to Clear a Persistent Pathogen" Nature Reviews vol. 12, pp. 750-764.
Barouch et al. 2014 "Immunologic Strategies for HIV-1 Remission and Eradication" Science 6193(345):169-174.
Barton et al. (2013) "Prospects for Treatment of Latent HIV" Clinical Pharmacology & Therapeutics 93(1): 46-56.
Battistini et al. (2014) "*HIV-1 Latency: An Update of Molecular Mechanisms and Therapeutic Strategies*" Viruses 6:1715-1758.
Cillo et al. (2014) "Quantification of HIV-1 latency reversal in resting CD4+ T cells from patients on suppressive antiretroviral therapy" PNAS 111(19): 7078-7083.
International Search Report—Written Opinion dated Apr. 6, 2017 for PCT/US2016/054516.
Marsden et al. (2014) "*Neutralizing the HIV Reservoir*" Department of Medicine, Div of Hematology and Oncology. UCLA AIDS Institute Cell(158): 971-972.
Miller et al. (2013) "Proteasome inhibitors act as bifunctional antagonists of human immunodeficiency virus type 1 latency and replication" Retrovirology 10(1): 1-15.
Murry et al. 2015 "Cyanotriazoles Activate Latent HIV and Strongly Synergize with Proteasome Inhibitors Ex Vivo in Resting CD4 T Cells from Suppressed HIV+ Donors" Powerpoint presentation.
Murry et al. (2015) "Cyanotriazoles activate latent HIV and strongly synergize with proteasome inhibitors ex vivo in resting CD4 T cells from suppressed HIV+ donors" Abstract.
Pan et al. (2016) "Heat Shock Protein 90 Facilitates Latent HIV Reactivation through Maintaining the Function of Positive Transcriptional Elongation Factor b (p-TEFb) under Proteasome Inhibition" The Journal of Biological Chemistry (291)50: 26177-26187.

* cited by examiner

*Primary Examiner* — Alicia L Otton

(57) ABSTRACT

Provided are compounds, compositions, combinations, kits, uses, and methods for treating HIV in a human being using such compounds or combinations with proteasome inhibitors.

51 Claims, No Drawings

COMPOUNDS AND COMBINATIONS FOR THE TREATMENT OF HIV

CROSS-REFERENCE TO RELATED APPLICATIONS

This application claims the benefit under 35 U.S.C. § 119(e) of U.S. Provisional Application Ser. 62/235,302, filed Sep. 30, 2015, the entirety of which is incorporated herein by reference.

FIELD OF THE INVENTION

Provided are compounds of Formula (I):

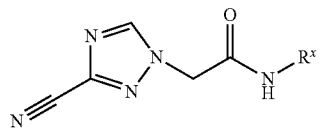

or pharmaceutically acceptable salts thereof, useful for treating HIV in a human.

Also provided are compositions, combinations, kits, uses, and methods for treating HIV in a human using such compounds or combinations with proteasome inhibitors.

BACKGROUND

Around the world more than thirty million people are infected by the HIV virus. Numerous drugs and combination therapies have been developed for the treatment of HIV infections in humans. While combination antiretroviral therapies (cART) and highly active antiretroviral therapies (HAART) have been able to reduce HIV viral loads, often below 50 copies of HIV RNA/ml of plasma, no therapy has provided elimination of HIV infected cells which are not actively replicating HIV, commonly referred to as a patient's latent reservoir of HIV. "Kick and kill" strategies have been proposed for reservoir reduction and/or elimination. Compounds with "kick" activity have the potential to reverse latency and increase HIV protein expression in infected cells, making them more susceptible to immune-mediated killing. Compounds with "kill" activity have the potential to enhance killing of HIV-infected cells, e.g. by enhancing immune effector cell function. "Kick" programs have tested various agents, including histone deacetylase inhibitors, disulfiram, PD-1 antibodies, and HIV vaccines, as noted in *Prospects for Treatment of Latent HIV*, Barton et al., Clin. Pharm. & Therap., Vol. 93, Issue 1, pp. 46-56; *Neutralizing the HIV Reservoir*, Marsden et al., Cell, 158, Aug. 28, 2014, pp. 971-972; HIV-1 *Latency: An Update of Molecular Mechanisms and Therapeutic Strategies*, Battistini et al., Viruses 2014, 6, 1715-1758; and Quantification of HIV-1 latency reversal in resting CD4+ T cells from patients on suppressive antiretroviral therapy, Cillo et al., PNAS, May 13, 2014, Vol. 111, No. 19, pp. 7078-7083.

There remains a need for new agents and therapies capable of assisting in the activation of the latent HIV-infected cells to enhance the activity of antiretroviral therapies and immune responses.

SUMMARY OF THE INVENTION

Provided herein are compounds of Formula (I)

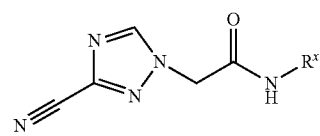

or a pharmaceutically acceptable salt thereof, wherein:
$R^x$ is selected from the group consisting of

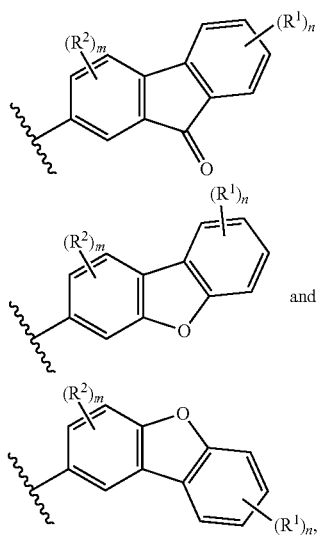

each $R^2$ is independently selected from the group consisting of halogen, $C_{1-6}$alkyl, $C_{2-6}$alkynyl, $C_{2-6}$alkenyl, $C_{1-6}$haloalkyl, $C_{1-6}$heteroalkyl, CN, $NR^aR^b$, $SR^a$ and $OR^a$, each $R^1$ is independently selected from the group consisting of halogen, $C_{1-6}$alkyl, $C_{1-6}$haloalkyl, $C_{1-6}$heteroalkyl, CN, $NH_2$, $NR^cR^d$, $SR^c$ and $OR^c$, each $R^a$ is independently selected from the group consisting of H, $C_{1-6}$alkyl, $C_{1-6}$haloalkyl, $C_{2-6}$alkynyl, and $C_{2-6}$alkenyl, each $R^b$ is independently selected from the group consisting of H, $C_{1-6}$alkyl, $C_{1-6}$haloalkyl, $C_{2-6}$alkynyl, and $C_{2-6}$alkenyl, each $R^c$ is independently selected from the group consisting of $C_{1-6}$alkyl, and $C_{1-6}$haloalkyl, each $R^d$ is independently selected from the group consisting of H, $C_{1-6}$alkyl, and $C_{1-6}$haloalkyl, n is 0, 1, 2, 3, or 4, and
m is 0, 1, 2, or 3,
provided that the compound is not

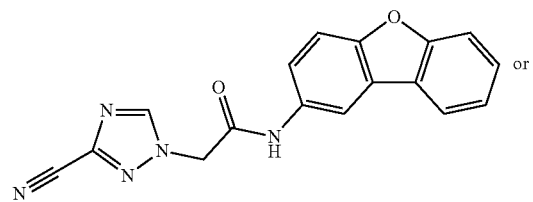

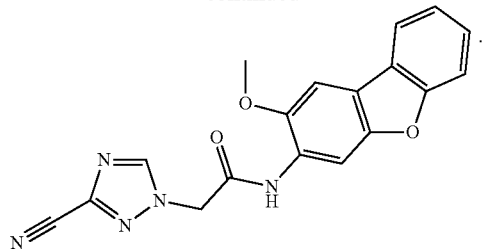

In certain embodiments, a pharmaceutically acceptable composition comprising a compound of Formula (I) or a compound of Formula:

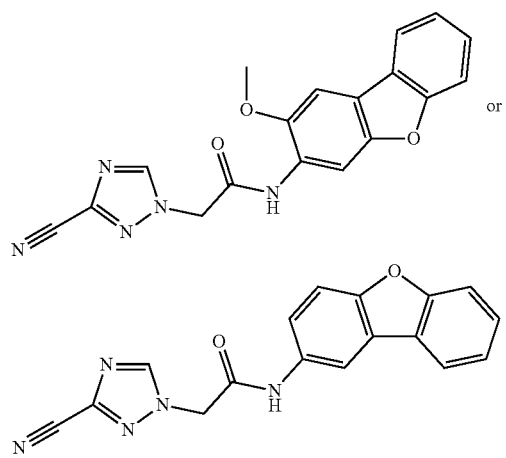

or a pharmaceutically acceptable salt thereof, is provided.

In certain embodiments, a method of treating an HIV infection in a human, the method comprising administering to a human in need thereof a pharmaceutically effective amount of a compound of Formula (I) or a compound of Formula:

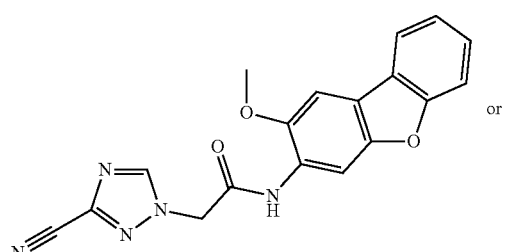

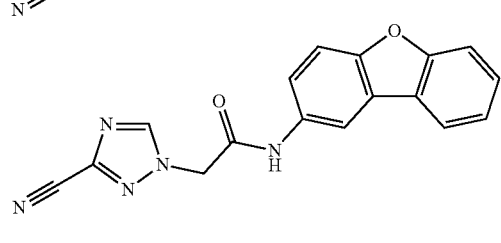

or a pharmaceutically acceptable salt thereof, is provided.

In certain embodiments, a method of inducing HIV gene expression in a human infected with HIV, the method comprising administering to the human infected with HIV a pharmaceutically effective amount of a compound of Formula (I) or a compound of Formula:

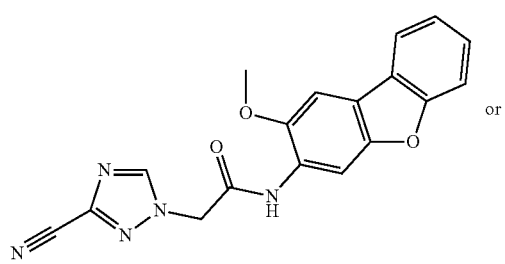

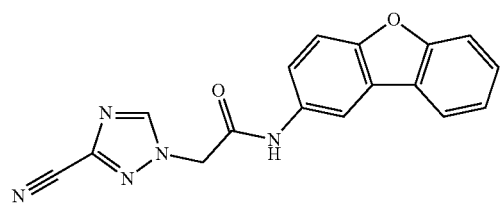

or a pharmaceutically acceptable salt thereof, is provided.

In certain embodiments, a method of reducing the latent HIV reservoir in a human infected with HIV, the method comprising administering to the human a pharmaceutically effective amount of a compound of Formula (I) or a compound of Formula:

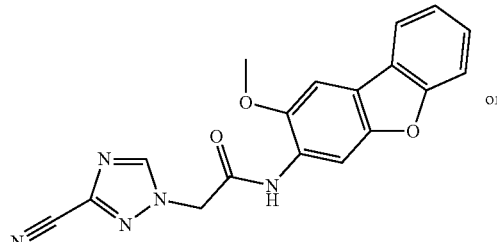

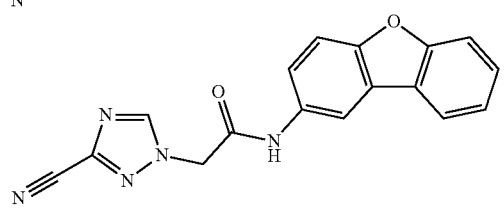

or a pharmaceutically acceptable salt thereof, is provided.

In certain embodiments, a pharmaceutically acceptable composition comprising a compound of Formula (I) or a compound of Formula:

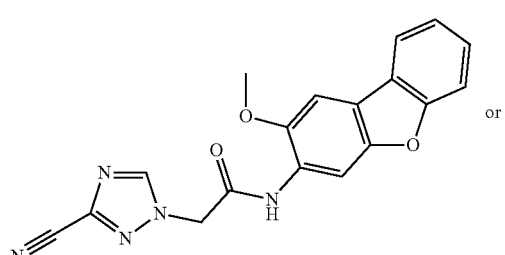

-continued

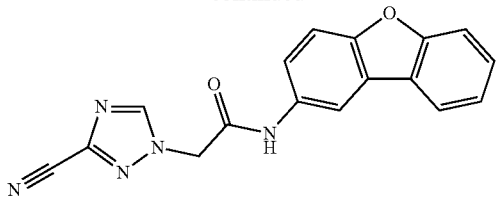

or a pharmaceutically acceptable salt thereof, and a proteasome inhibitor, or a pharmaceutically acceptable salt thereof, is provided.

In certain embodiments, a method of treating an HIV infection in a human, the method comprising administering to a human in need thereof a pharmaceutically effective amount of a compound of Formula (I) or a compound of Formula:

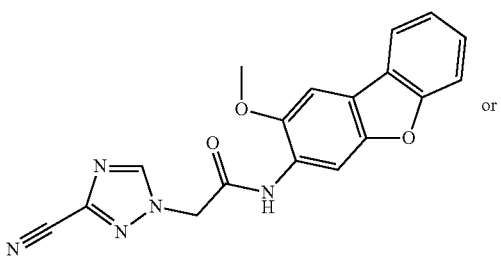

or

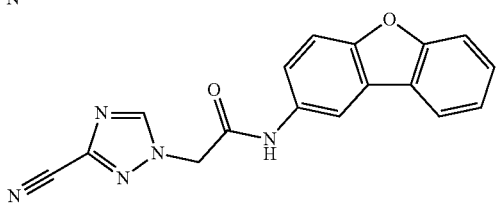

or a pharmaceutically acceptable salt thereof, and a pharmaceutically effective amount of a proteasome inhibitor, or a pharmaceutically acceptable salt thereof, is provided.

In certain embodiments, a method of inducing HIV gene expression in a human infected with HIV, the method comprising administering to the human infected with HIV a pharmaceutically effective amount of a compound of Formula (I) or a compound of Formula:

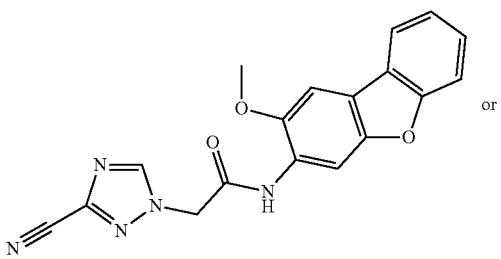

or

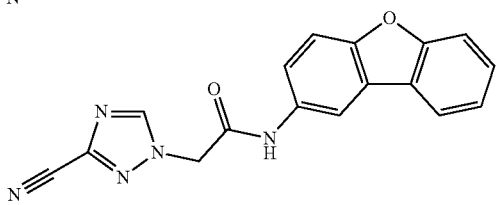

or a pharmaceutically acceptable salt thereof, and a pharmaceutically effective amount of a proteasome inhibitor, or a pharmaceutically acceptable salt thereof, is provided.

In certain embodiments, a method of reducing the latent HIV reservoir in a human infected with HIV, the method comprising administering to the human a pharmaceutically effective amount of a compound of Formula (I) or a compound of Formula:

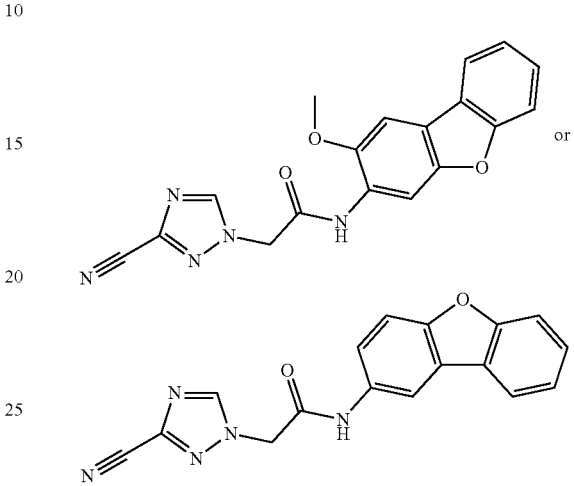

or a pharmaceutically acceptable salt thereof, and a pharmaceutically effective amount of a proteasome inhibitor, or a pharmaceutically acceptable salt thereof, is provided.

In certain embodiments, a method of eliminating an HIV infection in a human, the method comprising administering to a human in need thereof a pharmaceutically effective amount of a compound of Formula (I) or a compound of Formula:

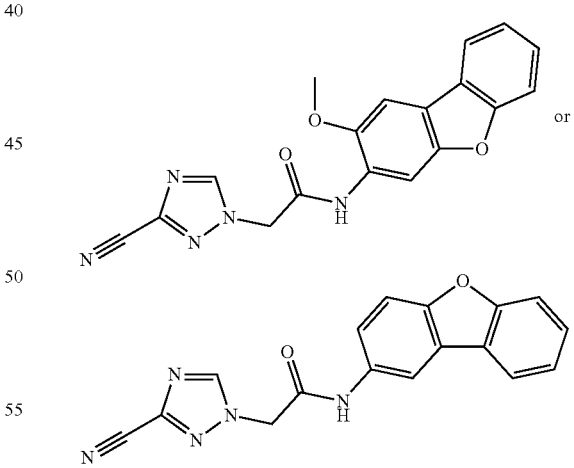

or a pharmaceutically acceptable salt thereof, and a pharmaceutically effective amount of a proteasome inhibitor, or a pharmaceutically acceptable salt thereof, is provided.

In certain embodiments, a method of reducing HIV viremia in a human infected with HIV, the method comprising administering to the human a pharmaceutically effective amount of a compound of Formula (I) or a compound of Formula:

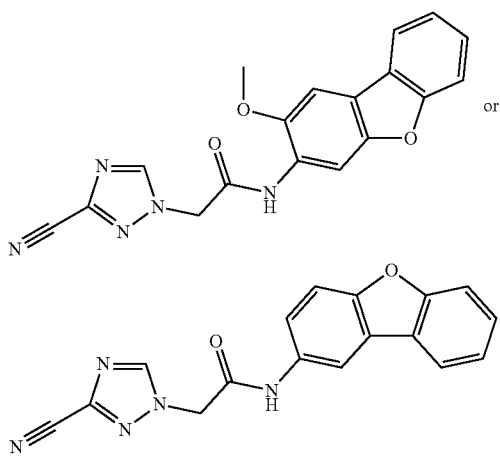

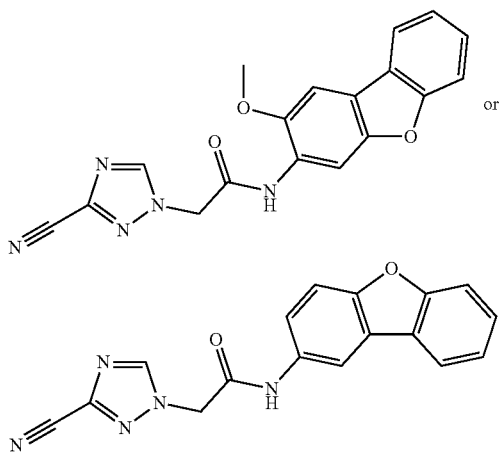

or a pharmaceutically acceptable salt thereof, and a pharmaceutically effective amount of a proteasome inhibitor, or a pharmaceutically acceptable salt thereof, is provided.

In certain embodiments, a kit comprising:

(1) a composition comprising a pharmaceutically effective amount of a compound of Formula (I) or a compound of Formula:

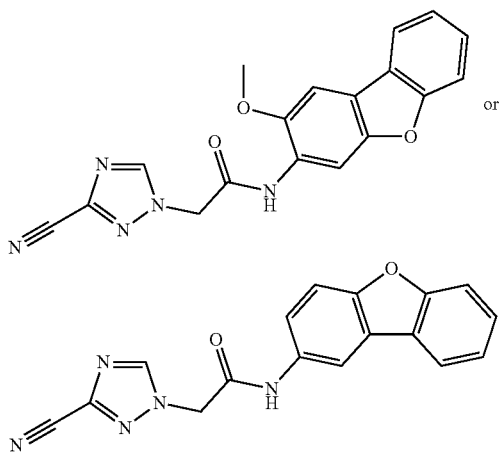

or a pharmaceutically acceptable salt thereof;

(2) a composition comprising a pharmaceutically effective amount of a proteasome inhibitor, or a pharmaceutically acceptable salt thereof; and (3) instructions for their co-administration, is provided.

In certain embodiments, a method of treating an HIV infection in a human, the method comprising:

a) administering to the human in need thereof a pharmaceutically effective amount of a combination antiretroviral therapy regimen sufficient to lower the level of HIV detected in the human's blood or plasma from a first level to a second level, the second level comprising a lower concentration of HIV in the human's blood or plasma than the concentration of HIV in the human's blood or plasma in the first level; and b) administering to the human a pharmaceutically effective amount of a compound of Formula (I) or a compound of Formula:

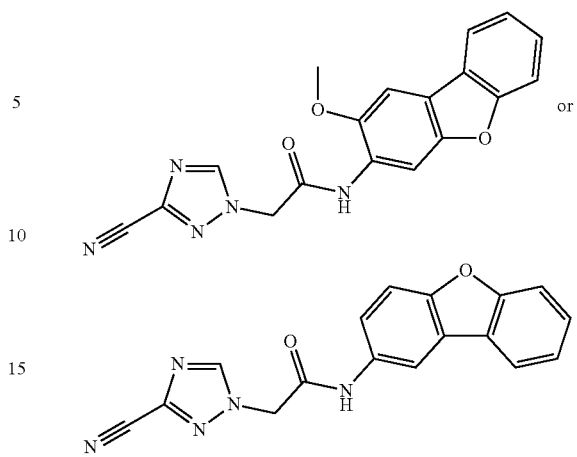

or a pharmaceutically acceptable salt thereof, and a pharmaceutically effective amount of a proteasome inhibitor, or a pharmaceutically acceptable salt thereof, is provided.

DETAILED DESCRIPTION

Definitions

"Therapeutically effective amount" or "effective amount" refers to that amount of the compound being administered which will prevent a condition, or will relieve to some extent one or more of the symptoms of the disorder being treated. Pharmaceutical compositions suitable for use herein include compositions wherein the active ingredients are contained in an amount sufficient to achieve the intended purpose. Determination of a therapeutically effective amount is well within the capability of those skilled in the art, especially in light of the detailed disclosure provided herein. As used herein, treatment refers to inhibition, reduction, elimination or alleviation of a disease as well as prevention.

The acronym "HIV" refers to the human immunodeficiency virus that causes acquired immunodeficiency syndrome, "AIDS".

The term "treating" and grammatical equivalents thereof, when used in the context of treating HIV, means slowing or stopping the progression of a disease; or ameliorating at least one symptom of a disease, more preferably ameliorating more than one symptom of a disease; or reducing the latent HIV reservoir.

The terms "combination antiretroviral therapy" ("cART") refers to combinations or "cocktails" of antiretroviral medications used to treat human viral infections, including HIV infections. As used herein, the terms "combination antiretroviral therapy" and "cART include combinations and regimens often referred to as Highly Active Antiretroviral Therapy (HAART). HAART and cART combinations and regimens commonly include multiple, often two or more, drugs such as nucleoside reverse transcriptase inhibitors (NRTIs), non-nucleoside reverse transcriptase inhibitors (NNRTIs), protease inhibitors (PIs), fusion inhibitors, CCR5 agonists, and/or integrase inhibitors.

The terms "latent HIV reservoir", " HIV latent reservoir", "HIV reservoir", "latent reservoir", and "latent HIV infection" refer to a condition in which resting CD4+ T lymphocytes or other cells are infected with HIV but are not actively producing HIV. The presently inactive HIV infected cells are referred to as "latently infected cells". Antiretroviral therapy (ART) can reduce the level of HIV in the blood to an undetectable level, while latent reservoirs of HIV continue to survive. When a latently infected cell is reactivated, the cell begins to produce HIV (HIV replication).

The term "pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes without limitation pharmaceutically-acceptable acid addition salts and pharmaceutically-acceptable base addition salts. Lists of suitable salts are found in, for example, S. M. Birge et al., J. Pharm. Sci., 1977, 66, pp. 1-19.

The terms "effective amount", "pharmaceutically effective amount", and "therapeutically effective amount" refer to an amount that may be effective to elicit the desired biological or medical response, including the amount of a compound that, when administered to a subject for treating a disease, is sufficient to effect such treatment for the disease. The effective amount will vary depending on the compound, the disease and its severity and the age, weight, etc., of the subject to be treated. The effective amount can include a range of amounts. A pharmaceutically effective amount includes amounts of an agent which are effective when combined with other agents.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals The terms "kit" and "pharmaceutical kit" refer to a commercial kit or package comprising, in one or more suitable containers, one or more pharmaceutical compositions and instructions for their use. Such kits may also be referred to by the terms "package" or "pharmaceutical package".

The terms "mL" and "ml" refer to milliliter.

The terms "antiviral agent", "antiretroviral agent", "antiretroviral compound" refer to a compounds or agent used to treat an HIV infection in a human.

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "$C_{u-v}$" or ($C_u$-$C_v$) indicates that the following group has from u to v carbon atoms, where u and v are integers. For example, "$C_{1-6}$alkyl" indicates that the alkyl group has from 1 to 6 carbon atoms.

"Alkyl" is a linear or branched saturated monovalent hydrocarbon. For example, an alkyl group can have 1 to 10 carbon atoms (i.e., ($C_{1-10}$)alkyl) or 1 to 8 carbon atoms (i.e., ($C_{1-8}$)alkyl) or 1 to 6 carbon atoms (i.e., ($C_{1-6}$ alkyl) or 1 to 4 carbon atoms (i.e., ($C_{1-4}$)alkyl). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (-($CH_2$)$_7CH_3$).

"Alkenyl" is a linear or branched monovalent hydrocarbon radical with at least one carbon-carbon double bond. For example, an alkenyl group can have 2 to 8 carbon atoms (i.e., $C_{2-8}$alkenyl), or 2 to 6 carbon atoms (i.e., $C_{2-6}$ alkenyl) or 2 to 4 carbon atoms (i.e., $C_{2-4}$ alkenyl). Examples of suitable alkenyl groups include, but are not limited to, ethylene or vinyl (—CH═$CH_2$), allyl (—$CH_2$CH═$CH_2$), 5-hexenyl (—$CH_2CH_2CH_2CH_2$CH═$CH_2$), and 3-hexenyl (—$CH_2CH_2$CH═CH$CH_2CH_3$).

"Alkynyl" is a linear or branched monovalent hydrocarbon radical with at least one carbon-carbon triple bond. For example, an alkynyl group can have 2 to 8 carbon atoms (i.e., $C_{2-8}$ alkyne,) or 2 to 6 carbon atoms (i.e., $C_{2-6}$ alkynyl) or 2 to 4 carbon atoms (i.e., $C_{2-4}$ alkynyl). Examples of alkynyl groups include, but are not limited to, acetylenyl (—C≡CH), propargyl (—$CH_2$C≡CH), and —$CH_2$—C≡C—$CH_3$.

The term "halo" or "halogen" as used herein refers to fluoro (—F), chloro (—Cl), bromo (—Br) and iodo (—I).

The term "haloalkyl" as used herein refers to an alkyl as defined herein, wherein one or more hydrogen atoms of the alkyl are independently replaced by a halo substituent, which may be the same or different. For example, $C_{1-8}$haloalkyl is a $C_{1-8}$alkyl wherein one or more of the hydrogen atoms of the $C_{1-8}$alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

The term "heteroalkyl" as used herein refers to an alkyl as defined herein, wherein one or more of the carbon atoms of the alkyl are replaced by an O, S, or $NR^q$, wherein each $R^q$ is independently H or $C_{1-6}$alkyl. For example, $C_{1-8}$heteroalkyl intends a heteroalkyl of one to eight carbons wherein one or more carbon atoms is replaced by a heteroatom (e.g., O, S, $NR^q$, OH, SH or $N(R^q)_2$), which may the same or different. Examples of heteroalkyls include but are not limited to methoxymethyl, ethoxymethyl, methoxy, 2-hydroxyethyl and N,N'-dimethylpropylamine. A heteroatom of a heteroalkyl may optionally be oxidized or alkylated. A heteroatom may be placed at any interior position of the heteroalkyl group or at a position at which the group is attached to the remainder of the molecule. Examples include, but are not limited to, —CH₂OCH₃, —CH₂CH₂NHCH₃, —CH₂CH₂N(CH₃)—CH₃, —CH₂SCH₂CH₃, —S(O)CH₃, —CH₂CH₂S(O)₂CH₃, —CHCHOCH₃, —CH₂CHNOCH₃, —CHCHN(CH₃)CH₃, —CH₂NHOCH₃ and —CH₂OS(CH₃)₃.

The embodiments disclosed herein are also meant to encompass all pharmaceutically acceptable compounds of Formula (I), or compound 1, or compound 2, or compound 3 or compound 4, being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formula (I), or compound 1, or compound 2, or compound 3 or compound 4, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I), or compound 1, or compound 2, or compound 3 or compound 4, can generally be prepared by conventional techniques known to those skilled in the art or by processes analogous to those described in the Examples as set out below using an appropriate isotopically-labeled reagent in place of the non-labeled reagent previously employed.

Provided herein are compounds of Formula (I)

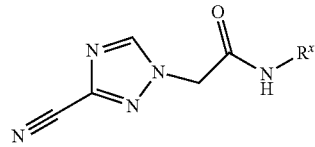

(I)

or a pharmaceutically acceptable salt thereof, wherein:
$R^x$ is selected from the group consisting of

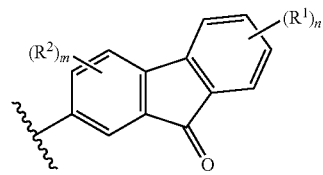

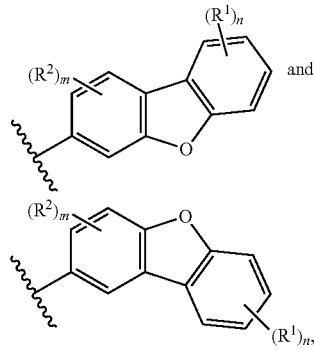
and each $R^2$ is independently selected from the group consisting of halogen, $C_{1-6}$alkyl, $C_{2-6}$alkynyl, $C_{2-6}$alkenyl, $C_{1-6}$haloalkyl, $C_{1-6}$heteroalkyl, CN, $NR^aR^b$, $SR^a$ and $OR^a$, each $R^1$ is independently selected from the group consisting of halogen, $C_{1-6}$alkyl, $C_{1-6}$haloalkyl, $C_{1-6}$heteroalkyl, CN, $NH_2$, $NR^cR^d$, $SR^c$ and $OR^c$, each $R^a$ is independently selected from the group consisting of H, $C_{1-6}$alkyl, $C_{1-6}$haloalkyl, $C_{2-6}$alkynyl, and $C_{2-6}$alkenyl, each $R^b$ is independently selected from the group consisting of H, $C_{1-6}$alkyl, $C_{1-6}$haloalkyl, $C_{2-6}$alkynyl, and $C_{2-6}$alkenyl, each $R^c$ is independently selected from the group consisting of $C_{1-6}$alkyl, and $C_{1-6}$haloalkyl, each $R^d$ is independently selected from the group consisting of H, $C_{1-6}$alkyl, and $C_{1-6}$haloalkyl, n is 0, 1, 2, 3, or 4, and
m is 0, 1, 2, or 3,
provided that the compound is not

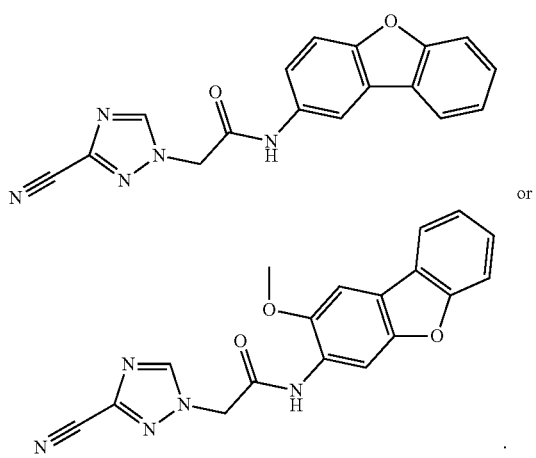

or

In certain embodiments, $R^x$ is

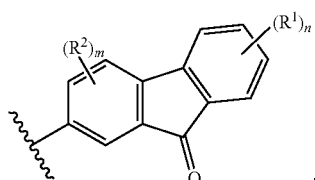

In certain embodiments, $R^x$ is

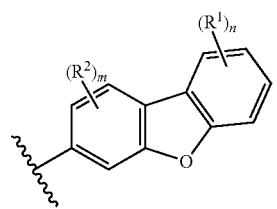

In certain embodiments, $R^x$ is

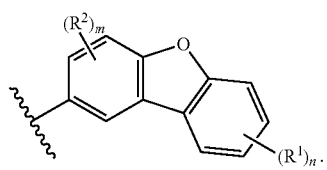

In certain embodiments, each $R^2$ is independently selected from the group consisting of halogen, $C_{1-6}$alkyl, $C_{1-6}$haloalkyl, and $OR^a$. In certain embodiments, each $R^2$ is independently selected from the group consisting of halogen, $C_{1-3}$alkyl, $C_{1-3}$haloalkyl, and $OR^a$. In certain embodiments, each $R^2$ is $OR^a$.

In certain embodiments, each $R^a$ is independently selected from the group consisting of H, $C_{1-6}$alkyl, and $C_{2-6}$alkynyl. In certain embodiments, each $R^a$ is independently selected from the group consisting of H, $C_{1-3}$alkyl, and $C_{2-3}$alkynyl. In certain embodiments, each $R^a$ is independently selected from the group consisting of methyl, and $C_3$alkynyl.

In certain embodiments, each $R^1$ is independently selected from the group consisting of halogen, $C_{1-6}$alkyl, $C_{1-6}$haloalkyl, CN, $NH_2$ and $OR^c$. In certain embodiments, each $R^1$ is independently selected from the group consisting of halogen, $C_{1-3}$alkyl, $C_{1-3}$haloalkyl, CN, $NH_2$ and $OR^c$. In certain embodiments, each $R^1$ is $OR^c$.

In certain embodiments, each $R^c$ is independently selected from the group consisting of $C_{1-6}$alkyl, and $C_{1-6}$haloalkyl. In certain embodiments, each $R^c$ is independently selected from the group consisting of $C_{1-3}$alkyl, and $C_{1-3}$haloalkyl. In certain embodiments, each $R^c$ is independently selected from the group consisting of methyl and $C_1$haloalkyl.

In certain embodiments, n is 0 or 1 and m is 0 or 1.
In certain embodiments, m=0.
In certain embodiments, n=0.
In certain embodiments, m=0 and n=0.
In certain embodiments, m=1 and $R^2$ is —$OR^a$.
In certain embodiments, m=1, $R^2$ is —$OR^a$ and n=0.
In certain embodiments, m=1, $R^2$ is —$OR^a$ and $R^a$ is independently selected from the group consisting of $C_{1-6}$alkyl, and $C_{2-6}$alkynyl. In certain embodiments, m=1, $R^2$ is —$OR^a$ and $R^a$ is independently selected from the group consisting of $C_{1-3}$alkyl, and $C_{2-3}$alkynyl. In certain embodiments, n=0, m=1, $R^2$ is —$OR^a$ and $R^a$ is independently selected from the group consisting of $C_{1-6}$alkyl, and $C_{2-6}$alkynyl. In certain embodiments, m=1, n=0, $R^2$ is —$OR^a$ and $R^a$ is independently selected from the group consisting of $C_{1-3}$alkyl, and $C_{2-3}$alkynyl.

In certain embodiments, m=1, $R^2$ is —$OR^a$ and $R^a$ is methyl or —$CH_2C≡CH$.

In certain embodiments, m=1, $R^2$ is —$OR^a$, $R^a$ is methyl or —$CH_2C≡CH$, and n=0.

In certain embodiments, compound (I) is selected from the group consisting of:

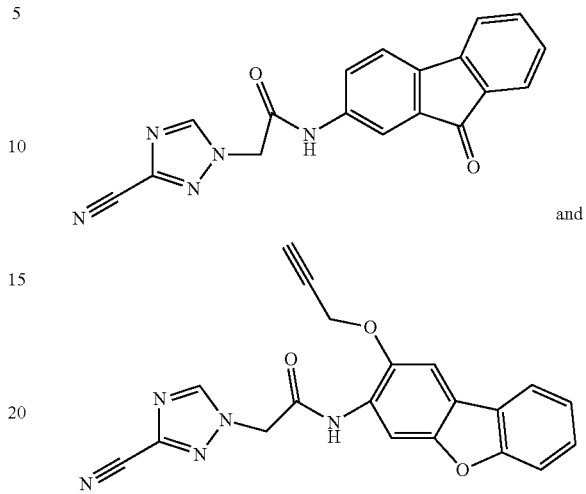

or a pharmaceutically acceptable salt thereof.

In certain embodiments, a pharmaceutically acceptable composition comprising a compound of Formula (I) or a compound of Formula:

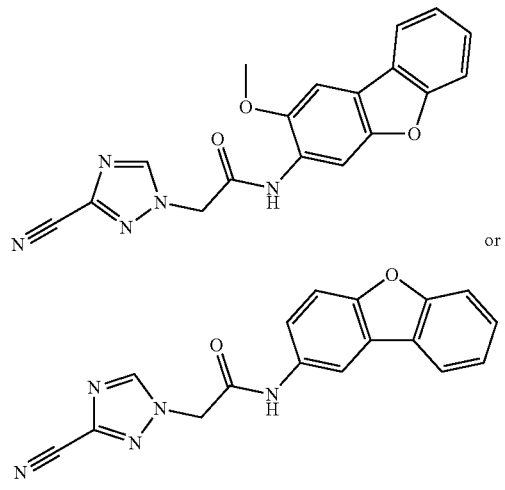

or a pharmaceutically acceptable salt thereof, is provided.

In certain embodiments, a pharmaceutically acceptable composition comprising a compound selected from the group consisting of:

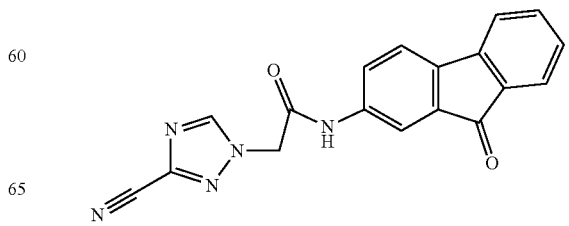

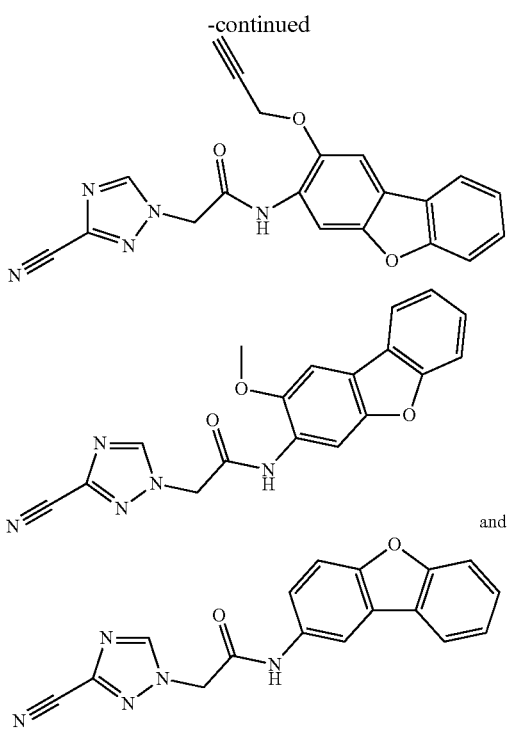

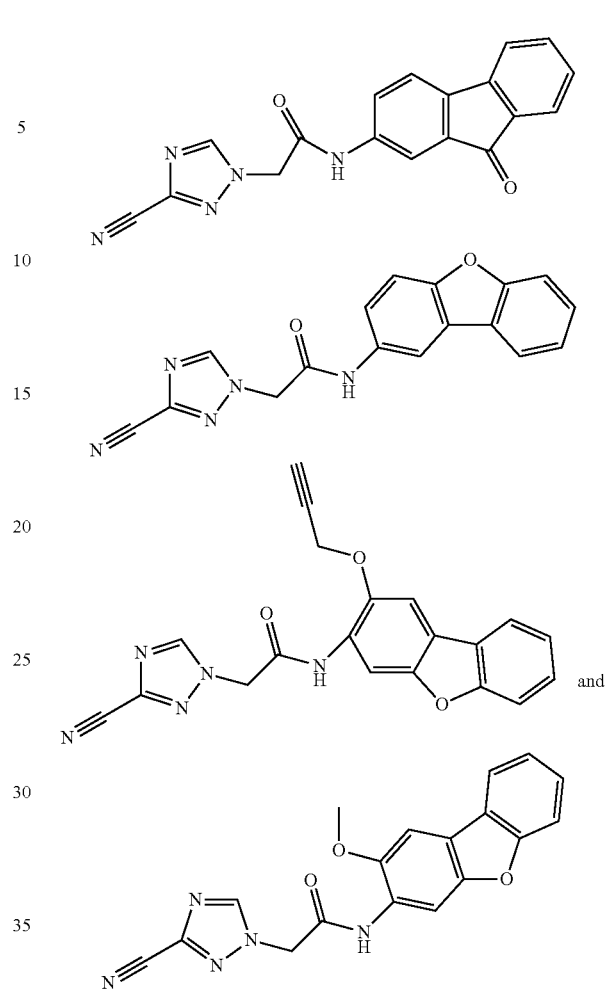

or a pharmaceutically acceptable salt thereof, is provided.

In certain embodiments, the composition further comprises one or more pharmaceutically acceptable excipients.

In certain embodiments, the composition further comprises one or more anti-HIV agents. In certain embodiments, the composition further comprises antiretroviral therapy agents (including combination antiretroviral therapy agents or "cART" agents).

In certain embodiments, a method of treating an HIV infection in a human, the method comprising administering to a human in need thereof a pharmaceutically effective amount of a compound of Formula (I) or a compound of Formula:

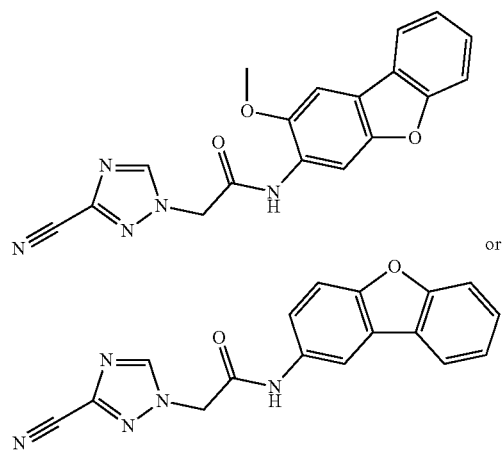

or a pharmaceutically acceptable salt thereof, is provided.

In certain embodiments, the method comprises administering a compound selected from the group consisting of:

or a pharmaceutically acceptable salt thereof.

In certain embodiments, the method further comprises administering one or more anti-HIV agents. In certain embodiments, the method further comprises administering antiretroviral therapy (including combination antiretroviral therapy" or "cART").

In certain embodiments, active HIV gene expression in the human has been suppressed by administration of antiretroviral therapy (including combination antiretroviral therapy" or "cART").

In certain embodiments, a method of inducing HIV gene expression in a human infected with HIV, the method comprising administering to the human infected with HIV a pharmaceutically effective amount of a compound of Formula (I) or a compound of Formula:

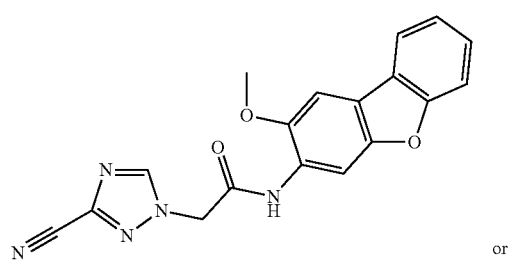

or

-continued

[chemical structure]

or a pharmaceutically acceptable salt thereof, is provided.

In certain embodiments, the method comprises administering a compound selected from the group consisting of:

[chemical structures]

or a pharmaceutically acceptable salt thereof.

In certain embodiments, the method further comprises administering one or more anti-HIV agents. In certain embodiments, the method further comprises administering antiretroviral therapy (including combination antiretroviral therapy" or "cART").

In certain embodiments, active HIV gene expression in the human has been suppressed by administration of antiretroviral therapy (including combination antiretroviral therapy" or "cART").

In certain embodiments, a method of reducing the latent HIV reservoir in a human infected with HIV, the method comprising administering to the human a pharmaceutically effective amount of a compound of Formula (I) or a compound of Formula:

[chemical structures]

or a pharmaceutically acceptable salt thereof, is provided.

In certain embodiments, the method comprises administering a compound selected from the group consisting of:

[chemical structures]

or a pharmaceutically acceptable salt thereof.

In certain embodiments, the method further comprises administering one or more anti-HIV agents. In certain embodiments, the method further comprises administering antiretroviral therapy (including combination antiretroviral therapy" or "cART").

In certain embodiments, active HIV gene expression in the human has been suppressed by administration of antiretroviral therapy (including combination antiretroviral therapy" or "cART").

In certain embodiments, a pharmaceutically acceptable composition comprising a compound of Formula (I) or a compound of Formula:

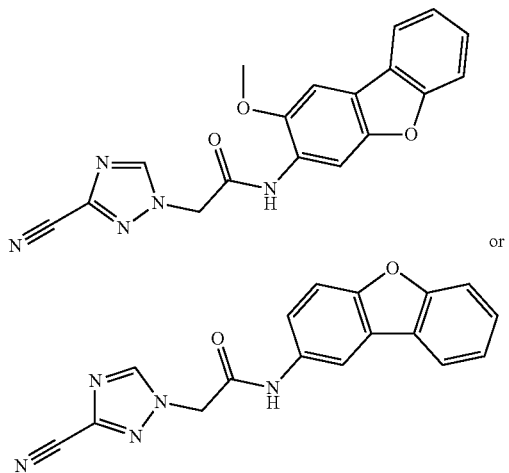

or a pharmaceutically acceptable salt thereof, and a proteasome inhibitor, or a pharmaceutically acceptable salt thereof, is provided.

In certain embodiments, the composition comprises a compound selected from the group consisting of:

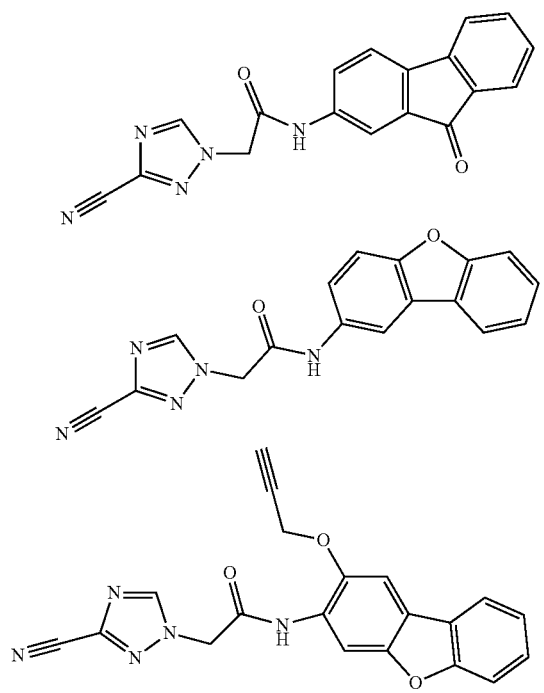

and

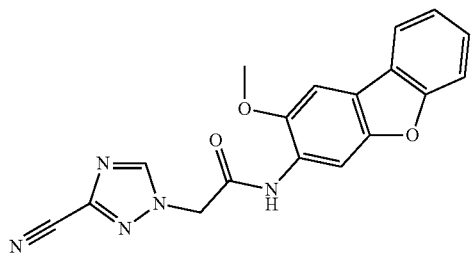

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, the composition further comprises one or more pharmaceutically acceptable excipients.

In certain embodiments, the composition further comprises one or more anti-HIV agents. In certain embodiments, the composition further comprises antiretroviral therapy agents (including combination antiretroviral therapy agents or "cART" agents).

In certain embodiments, a method of treating an HIV infection in a human, the method comprising administering to a human in need thereof a pharmaceutically effective amount of a compound of Formula (I) or a compound of Formula:

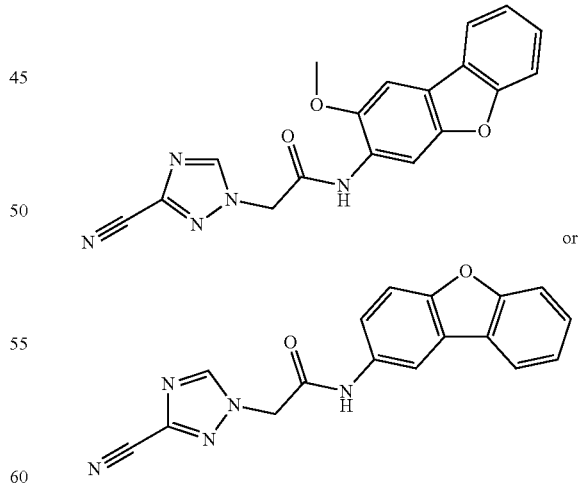

or a pharmaceutically acceptable salt thereof, and a pharmaceutically effective amount of a proteasome inhibitor, or a pharmaceutically acceptable salt thereof, is provided.

In certain embodiments, the method comprises administering a compound selected from the group consisting of:

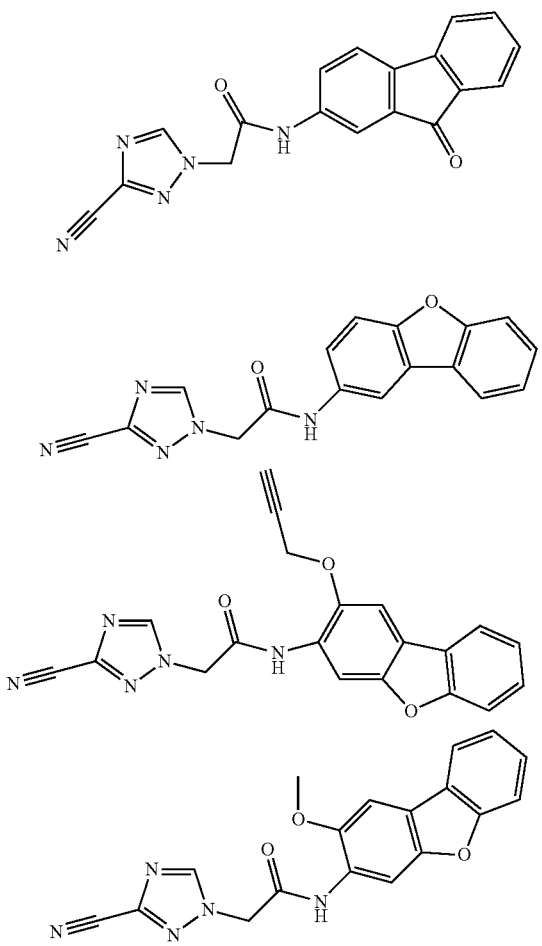

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, the method further comprises administering one or more anti-HIV agents. In certain embodiments, the method further comprises administering antiretroviral therapy (including combination antiretroviral therapy" or "cART").

In certain embodiments, active HIV gene expression in the human has been suppressed by administration of antiretroviral therapy (including combination antiretroviral therapy" or "cART").

In certain embodiments, a method of inducing HIV gene expression in a human infected with HIV, the method comprising administering to the human infected with HIV a pharmaceutically effective amount of a compound of Formula (I) or a compound of Formula:

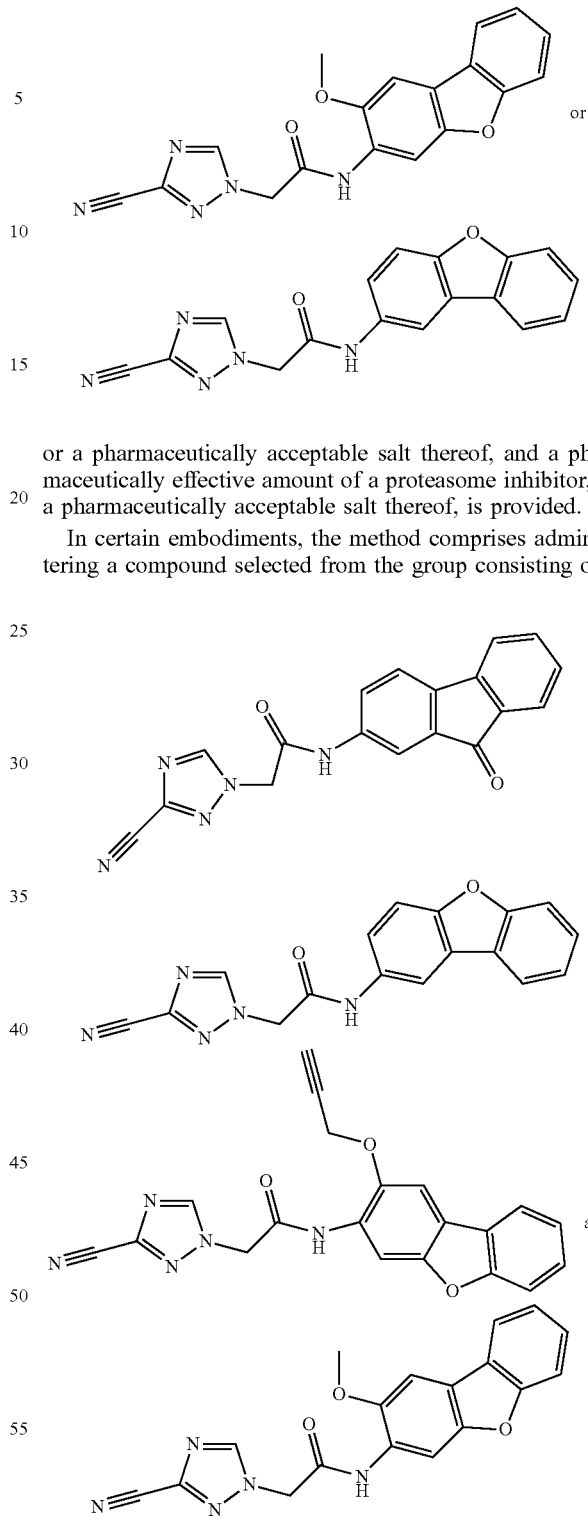

or a pharmaceutically acceptable salt thereof, and a pharmaceutically effective amount of a proteasome inhibitor, or a pharmaceutically acceptable salt thereof, is provided.

In certain embodiments, the method comprises administering a compound selected from the group consisting of:

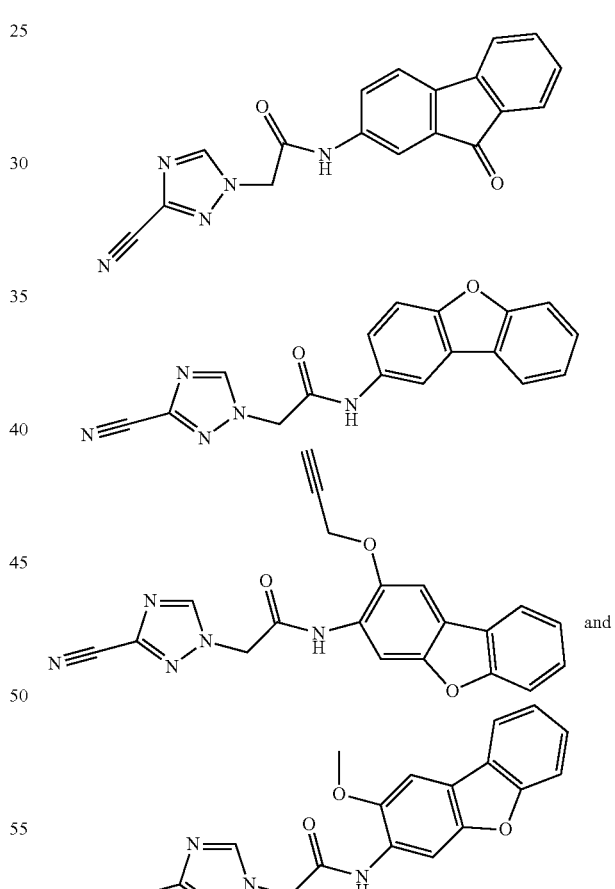

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, the method further comprises administering one or more anti-HIV agents. In certain embodiments, the method further comprises administering antiretroviral therapy (including combination antiretroviral therapy" or "cART").

In certain embodiments, active HIV gene expression in the human has been suppressed by administration of antiretroviral therapy (including combination antiretroviral therapy" or "cART").

In certain embodiments, a method of reducing the latent HIV reservoir in a human infected with HIV, the method comprising administering to the human a pharmaceutically effective amount of a compound of Formula (I) or a compound of Formula:

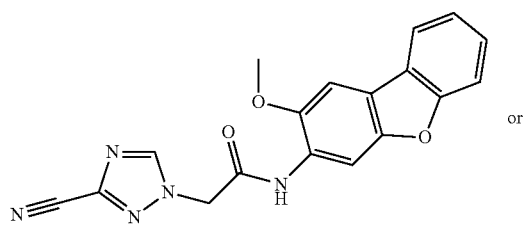

or

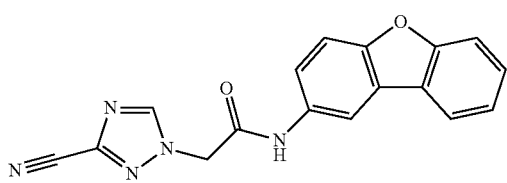

or a pharmaceutically acceptable salt thereof, and a pharmaceutically effective amount of a proteasome inhibitor, or a pharmaceutically acceptable salt thereof, is provided.

In certain embodiments, the method comprises administering a compound selected from the group consisting of:

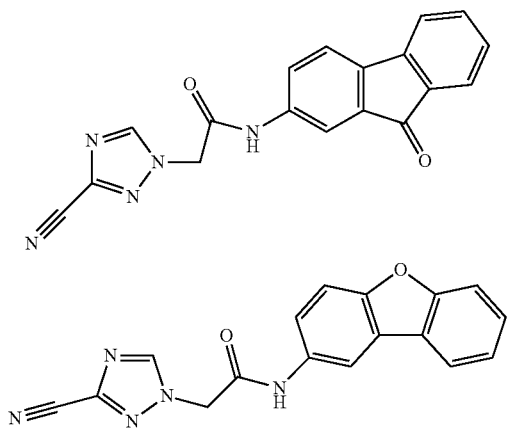

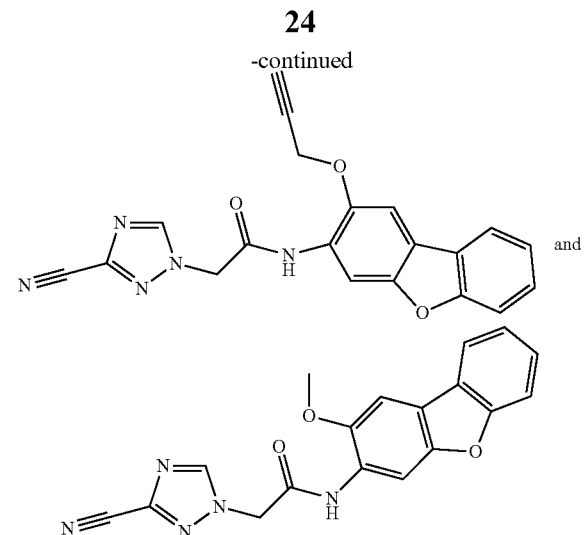

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, the method further comprises administering one or more anti-HIV agents. In certain embodiments, the method further comprises administering antiretroviral therapy (including combination antiretroviral therapy" or "cART").

In certain embodiments, active HIV gene expression in the human has been suppressed by administration of antiretroviral therapy (including combination antiretroviral therapy" or "cART").

In certain embodiments, a method of eliminating an HIV infection in a human, the method comprising administering to a human in need thereof a pharmaceutically effective amount of a compound of Formula (I) or a compound of Formula:

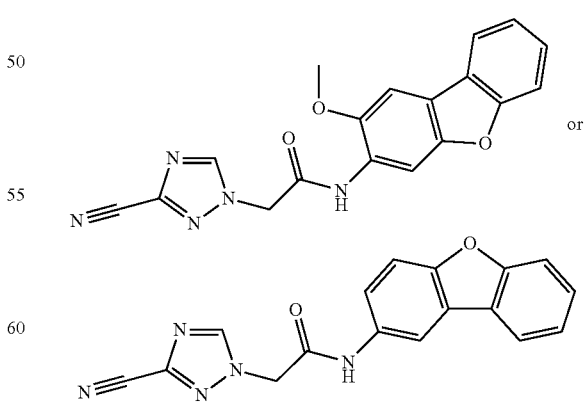

or a pharmaceutically acceptable salt thereof, and a pharmaceutically effective amount of a proteasome inhibitor, or a pharmaceutically acceptable salt thereof, is provided.

In certain embodiments, the method comprises administering a compound selected from the group consisting of:

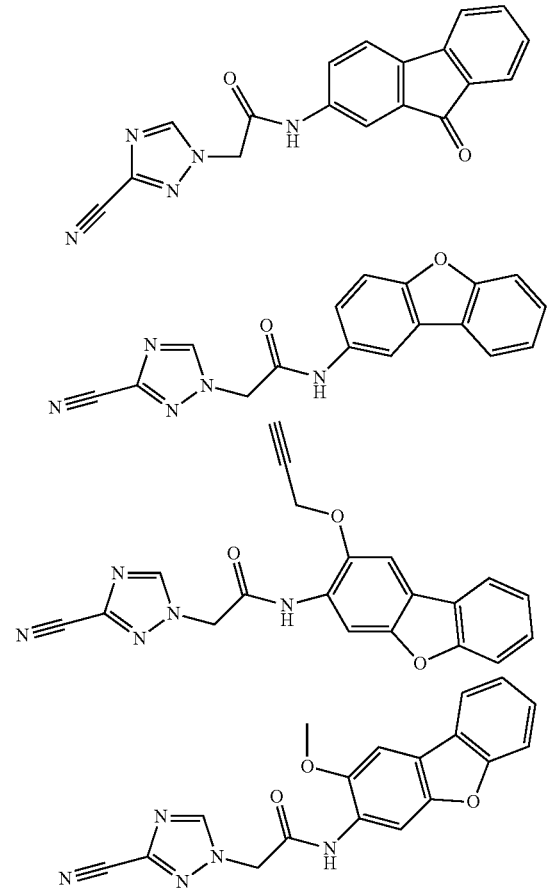

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, the method further comprises administering one or more anti-HIV agents. In certain embodiments, the method further comprises administering antiretroviral therapy (including combination antiretroviral therapy" or "cART").

In certain embodiments, active HIV gene expression in the human has been suppressed by administration of antiretroviral therapy (including combination antiretroviral therapy" or "cART").

In certain embodiments, a method of reducing HIV viremia in a human infected with HIV, the method comprising administering to the human a pharmaceutically effective amount of a compound of Formula (I) or a compound of Formula:

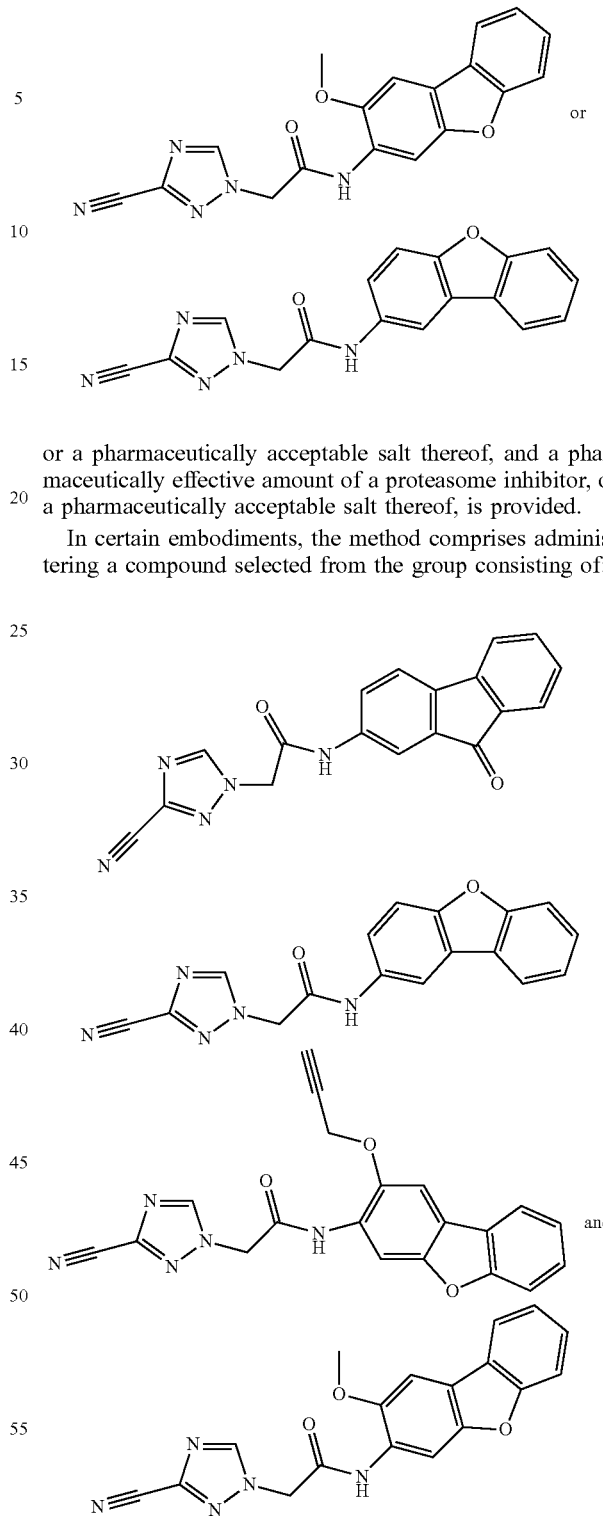

or a pharmaceutically acceptable salt thereof, and a pharmaceutically effective amount of a proteasome inhibitor, or a pharmaceutically acceptable salt thereof, is provided.

In certain embodiments, the method comprises administering a compound selected from the group consisting of:

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, the method further comprises administering one or more anti-HIV agents. In certain embodiments, the method further comprises administering antiretroviral therapy (including combination antiretroviral therapy" or "cART").

In certain embodiments, active HIV gene expression in the human has been suppressed by administration of antiretroviral therapy (including combination antiretroviral therapy" or "cART").

In certain embodiments, a kit comprising:

(1) a composition comprising a pharmaceutically effective amount of a compound of Formula (I) or a compound of Formula:

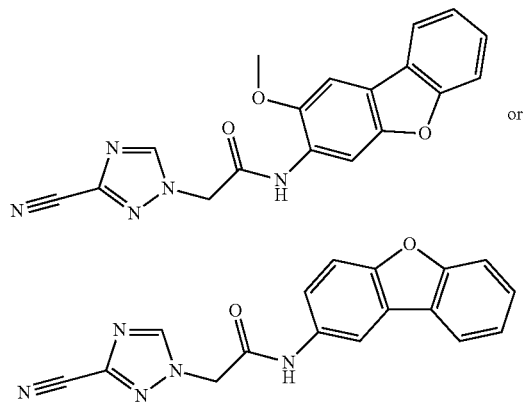

or a pharmaceutically acceptable salt thereof;

(2) a composition comprising a pharmaceutically effective amount of a proteasome inhibitor, or a pharmaceutically acceptable salt thereof; and (3) instructions for their co-administration, is provided.

In certain embodiments, the compound is selected from the group consisting of:

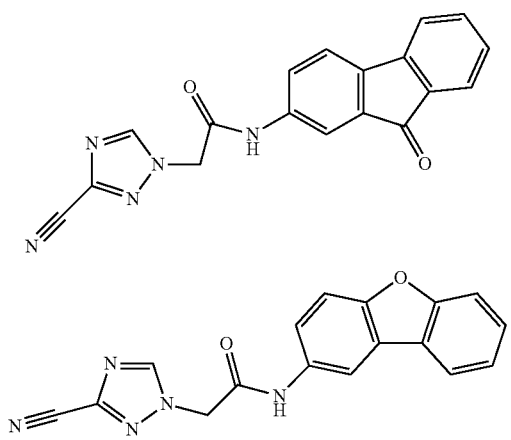

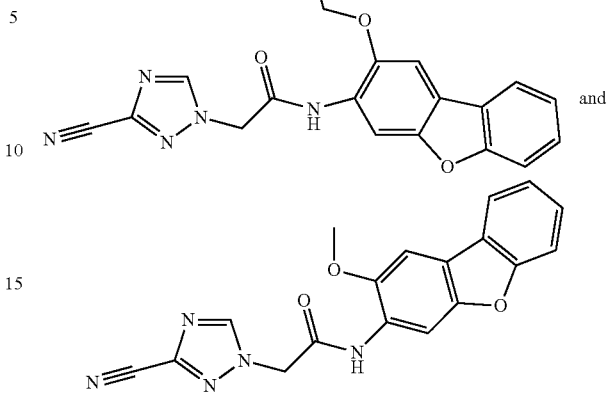

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, the method further comprises administering one or more anti-HIV agents. In certain embodiments, the method further comprises administering antiretroviral therapy (including combination antiretroviral therapy" or "cART").

In certain embodiments, active HIV gene expression in the human has been suppressed by administration of antiretroviral therapy (including combination antiretroviral therapy" or "cART").

In certain embodiments, a method of treating an HIV infection in a human, the method comprising:

a) administering to the human in need thereof a pharmaceutically effective amount of a combination antiretroviral therapy regimen sufficient to lower the level of HIV detected in the human's blood or plasma from a first level to a second level, the second level comprising a lower concentration of HIV in the human's blood or plasma than the concentration of HIV in the human's blood or plasma in the first level; and b) administering to the human a pharmaceutically effective amount of a compound of Formula (I) or a compound of Formula:

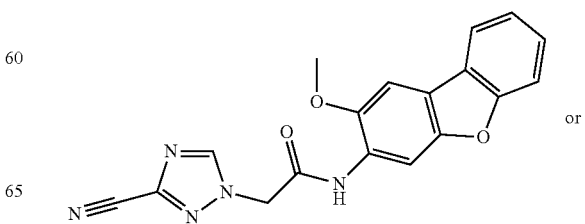

-continued

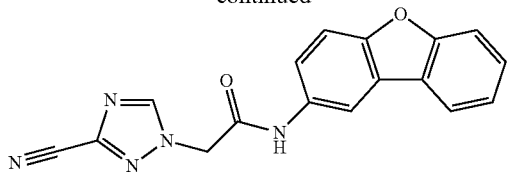

or a pharmaceutically acceptable salt thereof, and a pharmaceutically effective amount of a proteasome inhibitor, or a pharmaceutically acceptable salt thereof, is provided.

In certain embodiments, the compound is selected from the group consisting of

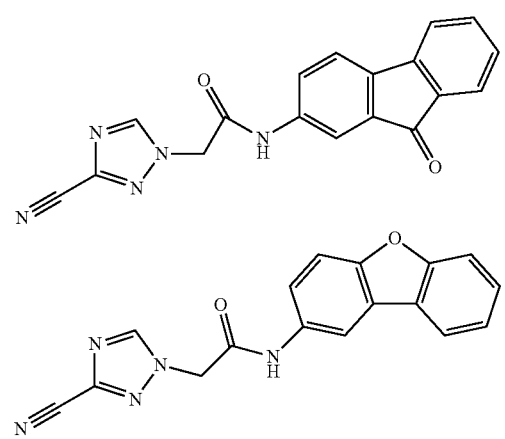

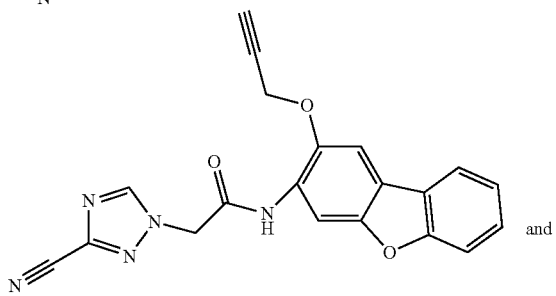 and

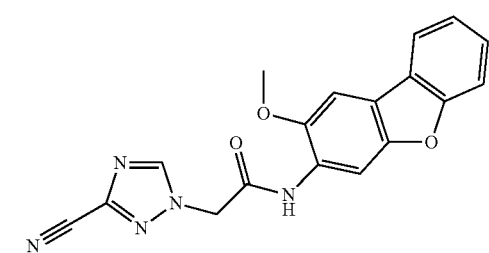

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, step a) and step b) are conducted sequentially.

In certain embodiments, step a) and step b) are conducted simultaneously.

In certain embodiments, use of a pharmaceutically effective amount of a compound of Formula (I) or a compound of Formula:

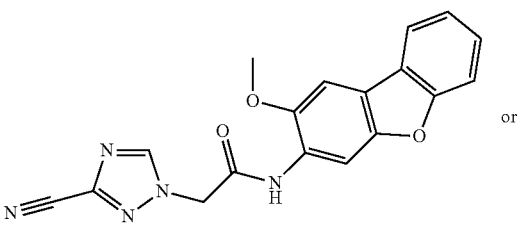 or

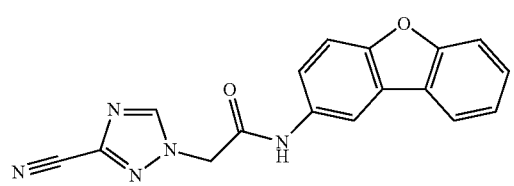

or a pharmaceutically acceptable salt thereof, and a pharmaceutically effective amount of a proteasome inhibitor, or a pharmaceutically acceptable salt thereof, for the treatment of an HIV infection in a human in need thereof, is provided.

In certain embodiments, the compound is selected from the group consisting of:

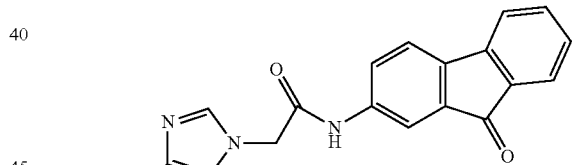

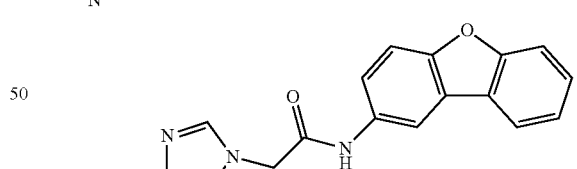

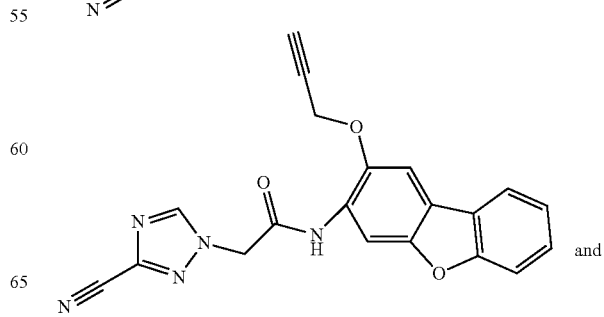 and

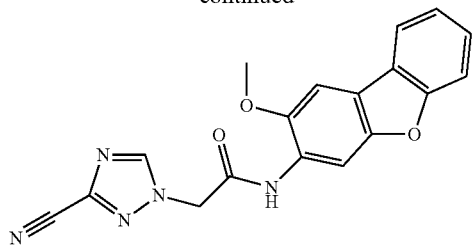

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, use of a pharmaceutically effective amount of a compound of Formula (I) or a compound of Formula:

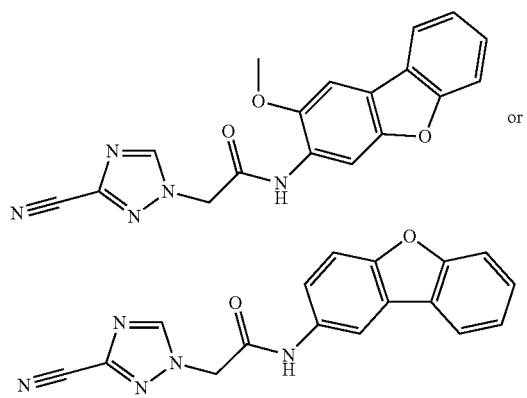

or or a pharmaceutically acceptable salt thereof, and a pharmaceutically effective amount of a proteasome inhibitor, or a pharmaceutically acceptable salt thereof, for the manufacture of a medicament for treating HIV in a human in need thereof, is provided.

In certain embodiments, the compound is selected from the group consisting of:

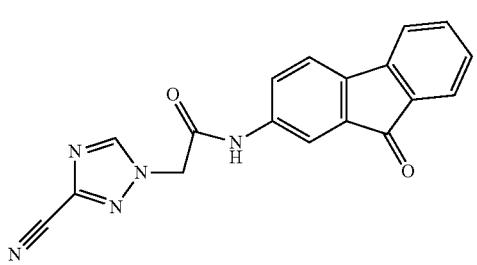

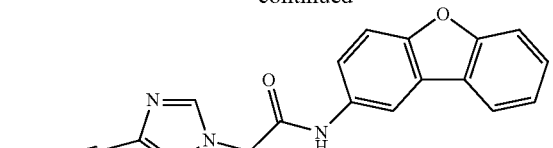

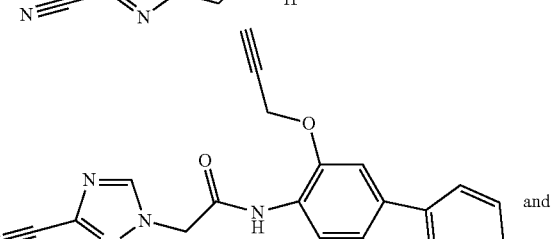

and

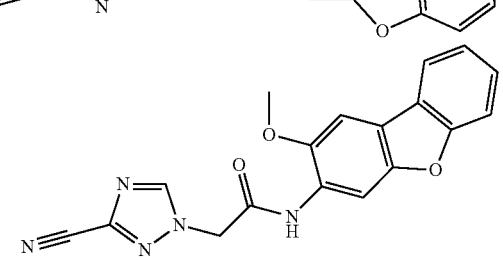

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, use of a pharmaceutically effective amount of a compound of Formula (I) or a compound of Formula:

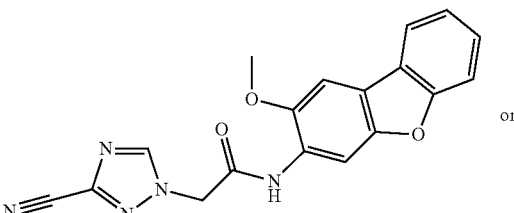

or

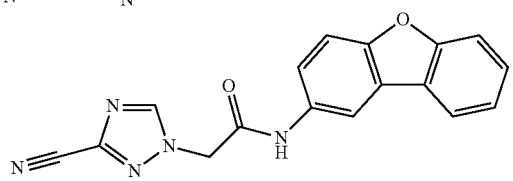

or a pharmaceutically acceptable salt thereof, and a pharmaceutically effective amount of a proteasome inhibitor, or a pharmaceutically acceptable salt thereof, for inducing HIV gene expression in a human infected with HIV, is provided.

In certain embodiments, the compound is selected from the group consisting of:

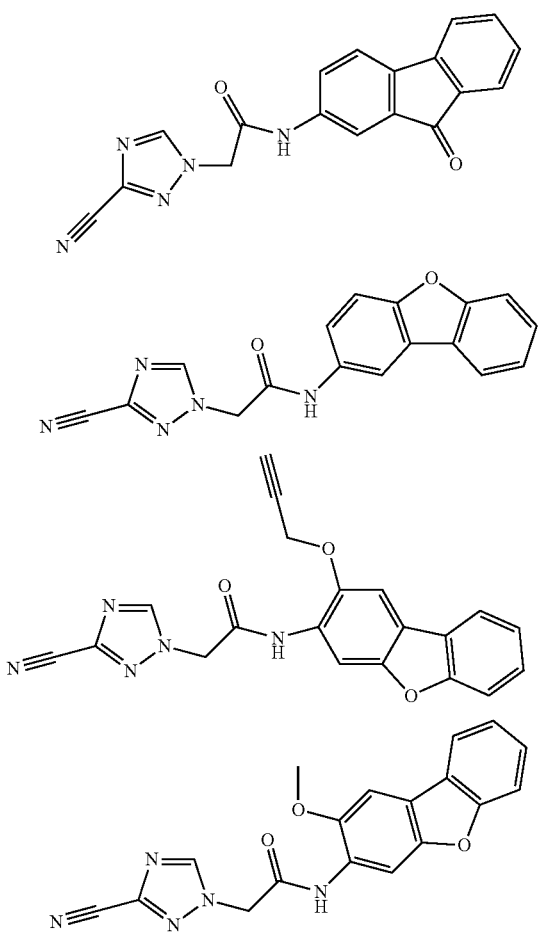

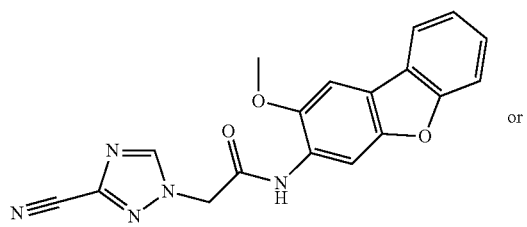

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, use of a pharmaceutically effective amount of a compound of Formula (I) or a compound of Formula:

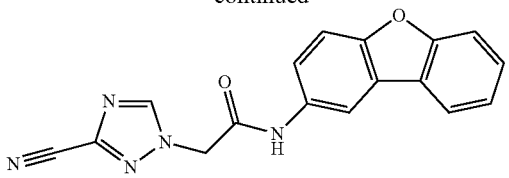

or a pharmaceutically acceptable salt thereof, and a pharmaceutically effective amount of a proteasome inhibitor, or a pharmaceutically acceptable salt thereof, for reducing the latent HIV reservoir in a human infected with HIV, is provided.

In certain embodiments, the compound is selected from the group consisting of:

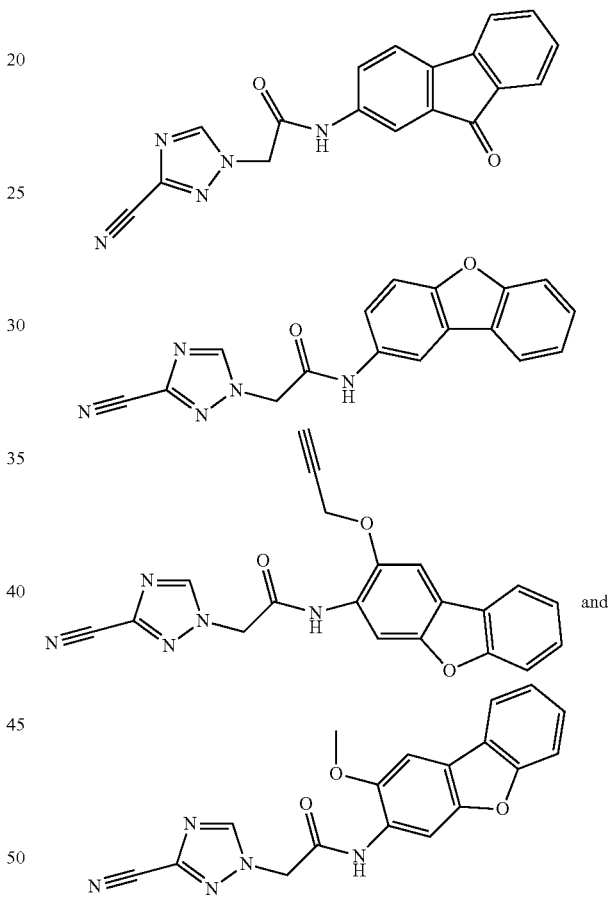

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, use of a pharmaceutically effective amount of a compound of Formula (I) or a compound of Formula:

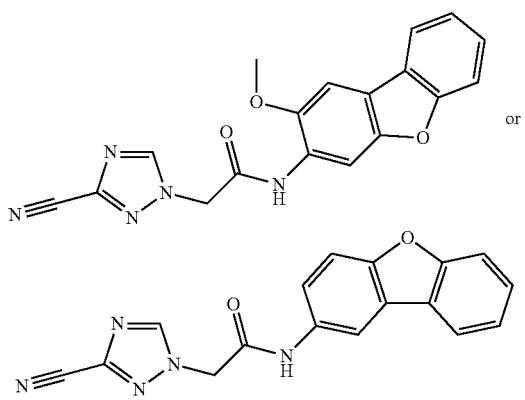

or a pharmaceutically acceptable salt thereof, and a pharmaceutically effective amount of a proteasome inhibitor, or a pharmaceutically acceptable salt thereof, for eliminating an HIV infection in a human, is provided.

In certain embodiments, the compound is selected from the group consisting of:

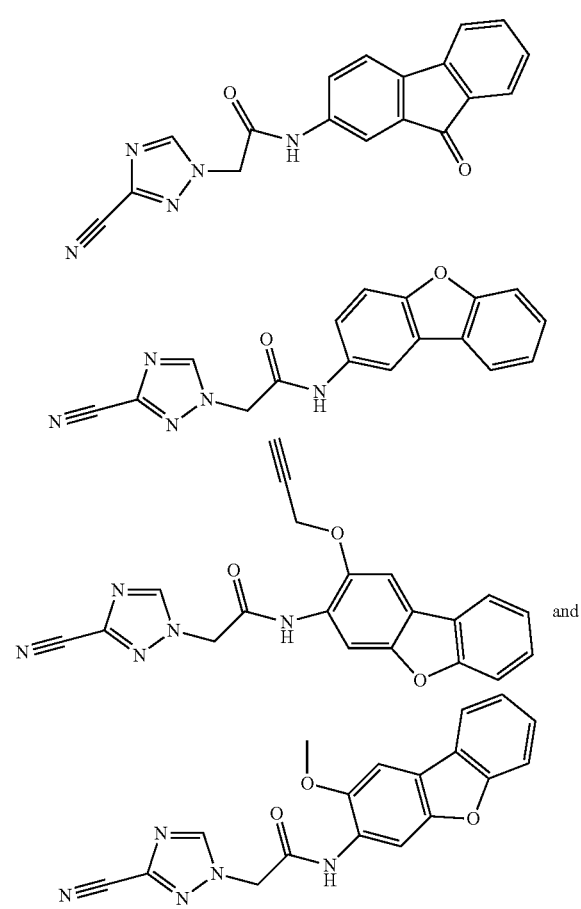

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, use of:

a) a pharmaceutically effective amount of a combination antiretroviral therapy regimen sufficient to lower the level of HIV detected in the human's blood or plasma from a first level to a second level, the second level comprising a lower concentration of HIV in the human's blood or plasma than the concentration of HIV in the human's blood or plasma in the first level; and b) a pharmaceutically effective amount of a compound of Formula (I) or a compound of Formula:

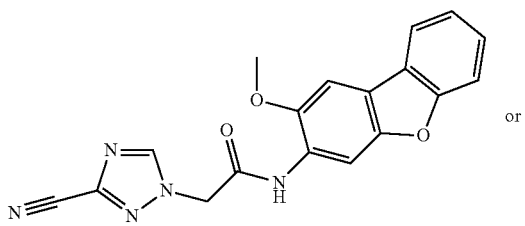

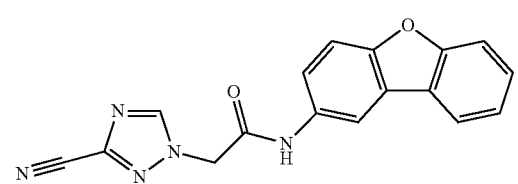

or a pharmaceutically acceptable salt thereof, and a pharmaceutically effective amount of a proteasome inhibitor, or a pharmaceutically acceptable salt thereof;

for treating an HIV infection in a human, is provided.

In certain embodiments, the compound is selected from the group consisting of

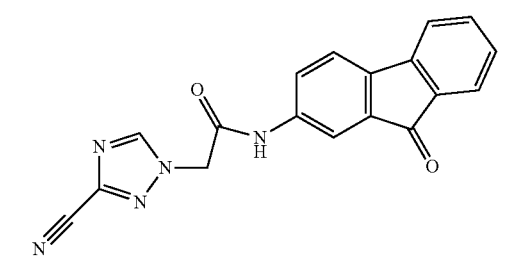

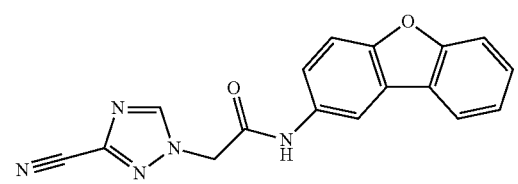

-continued

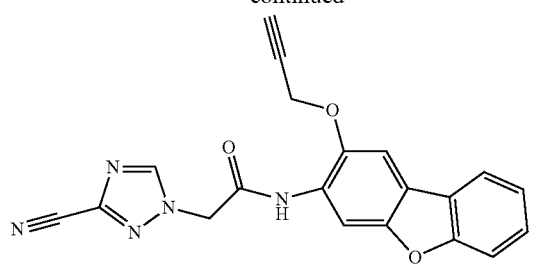
and

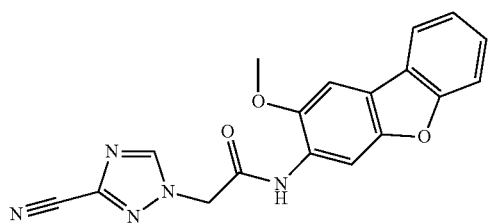

or a pharmaceutically acceptable salt thereof.

In certain embodiments, the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

In certain embodiments, the proteasome inhibitor is selected from the group consisting of bortezomib, carfilzomib, and oprozomib, or a pharmaceutically acceptable salt thereof. In certain embodiments, the proteasome inhibitor is bortezomib or a pharmaceutically acceptable salt thereof.

In certain embodiments, a) is administered before b).

In certain embodiments, a) and b) are administered simultaneously.

In certain embodiments, use of a pharmaceutically effective amount of a compound of Formula (I) or a compound of Formula:

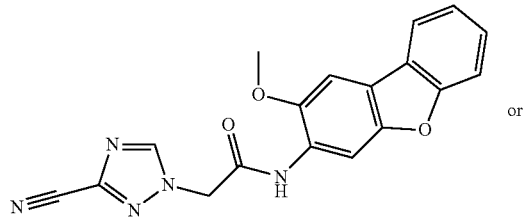

or a pharmaceutically acceptable salt thereof, for treating an HIV infection in a human, is provided.

In certain embodiments, the compound is selected from the group consisting of:

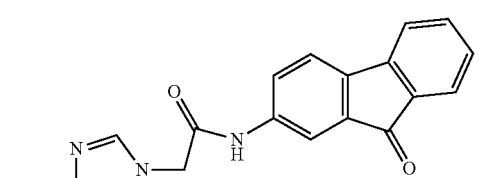

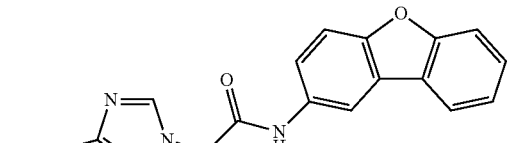

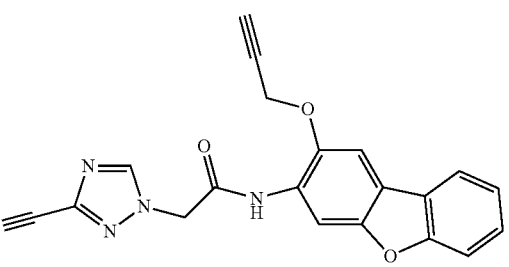
and

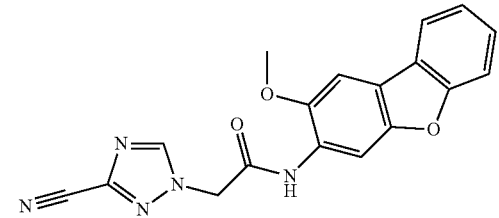

or a pharmaceutically acceptable salt thereof.

In certain embodiments, use of a pharmaceutically effective amount of a compound of Formula (I) or a compound of Formula:

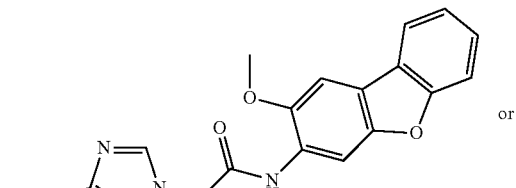
or

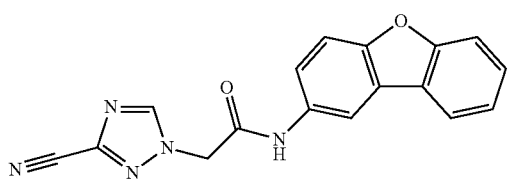

or a pharmaceutically acceptable salt thereof, for inducing HIV gene expression in a human infected with HIV, is provided.

In certain embodiments, the compound is selected from the group consisting of:

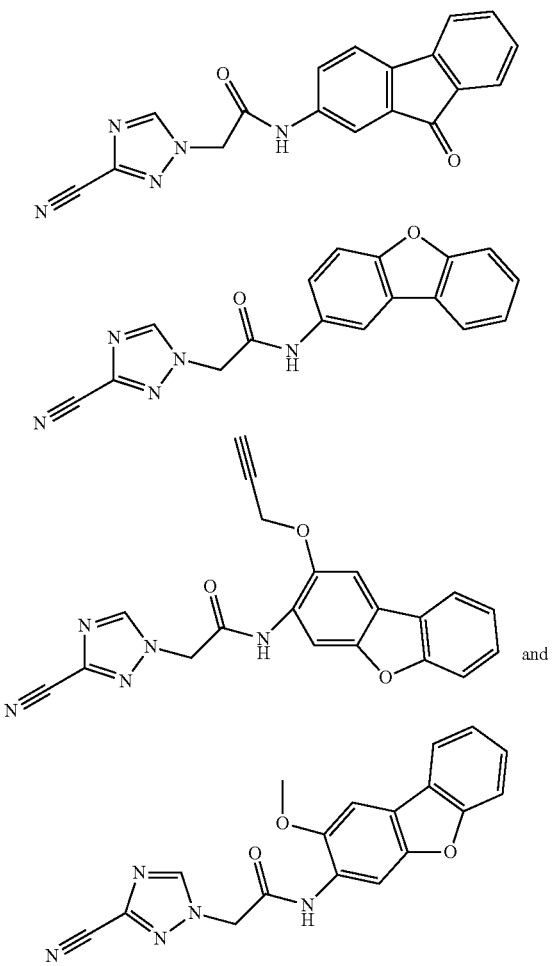

or a pharmaceutically acceptable salt thereof.

In certain embodiments, use of a pharmaceutically effective amount of a compound of Formula (I) or a compound of Formula:

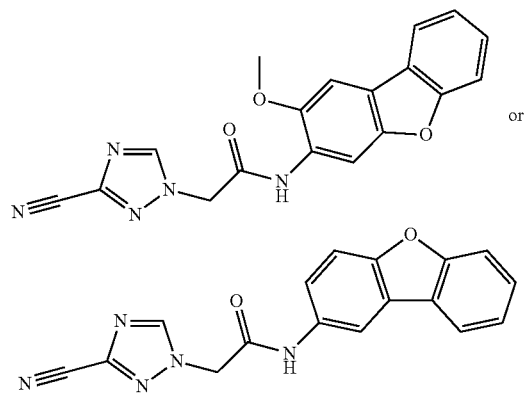

or a pharmaceutically acceptable salt thereof, for reducing the latent HIV reservoir in a human infected with HIV, is provided.

In certain embodiments, the compound is selected from the group consisting of:

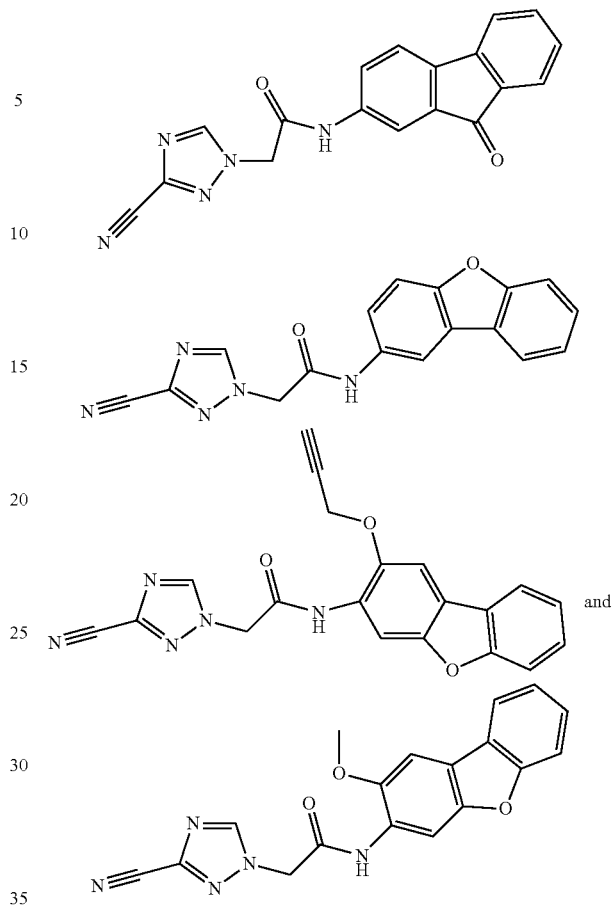

or a pharmaceutically acceptable salt thereof.

Provided are also pharmaceutically acceptable salts, hydrates, solvates, and tautomeric forms of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The active agents may be administered to a human in any conventional manner. While it is possible for the active agents to be administered as compounds, they are preferably administered as a pharmaceutical composition, which can include contact with an acid or base, either in an ionic salt form or in contact with the base or acid (i.e. co-formers) without sharing ions. The salt, acid or base co-former, carrier, or diluent should be acceptable in the sense of being compatible with the other ingredients and not deleterious to the recipient thereof. Examples of carriers or diluents for oral administration include cornstarch, lactose, magnesium stearate, talc, microcrystalline cellulose, stearic acid, povidone, crospovidone, dibasic calcium phosphate, sodium starch glycolate, hydroxypropyl cellulose (e.g., low substituted hydroxypropyl cellulose), hydroxypropylmethyl cellulose (e.g., hydroxypropylmethyl cellulose 2910), sodium lauryl sulfate, mannitol, sodium stearyl fumarate, and talc. Examples of salts and acid or base co-formers include fumarate, hemifumarate, sodium, hydrochloride and the like.

The pharmaceutical compositions may be prepared by any suitable method, such as those methods well known in the art of pharmacy, for example, methods such as those described in Gennaro et al., Remington's Pharmaceutical Sciences (18th ed., Mack Publishing Co., 1990), especially Part 8: Pharmaceutical Preparations and their Manufacture. Such methods include the step of bringing into association the compounds with the carrier or diluent and optionally one or more accessory ingredients. Such accessory ingredients include those conventional in the art, such as, fillers, binders, excipients, disintegrants, lubricants, colorants, flavoring agents, sweeteners, preservatives (e.g., antimicrobial preservatives), suspending agents, thickening agents, emulsifying agents, and/or wetting agents.

In practice, the amount of each compound to be administered ranges from about 0.001 to 100 mg per kg of body weight, such total dose being given at one time or in divided doses. Each compound will be administered as a formulation in association with one or more pharmaceutically acceptable excipients. Alternatively, both compounds will be combined and administered as a formulation in association with one or more pharmaceutically acceptable excipients. The choice of excipient will to a large extent depend on factors such as the particular mode of administration, the effect of the excipient on solubility and stability, and the nature of the dosage form.

Pharmaceutical compositions suitable for the delivery of compounds described herein and methods for their preparation will be readily apparent to those skilled in the art. Such compositions and methods for their preparation may be found, for example, in Remington's Pharmaceutical Sciences, 19th Edition (Mack Publishing Company, 1995).

One or more compounds of the invention (a compound of Formula (I), or compound 1, or compound 2, or compound 3 or compound 4, or a pharmaceutically acceptable salt thereof, with or without a proteasome inhibitor, or a pharmaceutically acceptable salt thereof) are administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with for example the condition of the recipient. In certain embodiments, the compound of Formula (I), or compound 1, or compound 2, or compound 3 or compound 4, or a pharmaceutically acceptable salt thereof, is administered orally while the proteasome inhibitor, or a pharmaceutically acceptable salt thereof, is administered parenterally (subcutaneously, intramuscularly, intravenously, intradermally, or intrathecally). Administration can be simultaneous or not.

In certain embodiments, a method for treating an HIV infection in a human having or at risk of having the infection is provided, comprising administering to the human a therapeutically effective amount of a compound of Formula (I), or compound 1, or compound 2, or compound 3 or compound 4, or a pharmaceutically acceptable salt thereof, with or without a proteasome inhibitor, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound of Formula (I), or compound 1, or compound 2, or compound 3 or compound 4, or a pharmaceutically acceptable salt thereof, with or without a proteasome inhibitor, or a pharmaceutically acceptable salt thereof, in combination with a therapeutically effective amount of one or more (e.g., one, two, three, one or two, or one to three) additional therapeutic agents.

In one embodiment, pharmaceutical compositions comprising a compound of Formula (I), or compound 1, or compound 2, or compound 3 or compound 4, or a pharmaceutically acceptable salt thereof, with or without a proteasome inhibitor, or a pharmaceutically acceptable salt thereof, in combination with one or more (e.g., one, two, three, one or two, or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound of Formula (I), or compound 1, or compound 2, or compound 3 or compound 4, or a pharmaceutically acceptable salt thereof, with or without a proteasome inhibitor, or a pharmaceutically acceptable salt thereof, in combination with a therapeutically effective amount of one or more additional therapeutic agents which are suitable for treating an HIV infection.

In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is combined with one, two, three, four, or more additional therapeutic agents. In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is combined with one additional therapeutic agents. In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is combined with two additional therapeutic agents. In other embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is combined with three additional therapeutic agents. In further embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered with one or more additional therapeutic agents. Co-administration of a compound of Formula (I), or compound 1, or compound 2, or compound 3 or compound 4, or a pharmaceutically acceptable salt thereof, with or without a proteasome inhibitor, or a pharmaceutically acceptable salt thereof, with one or more additional therapeutic agents generally refers to simultaneous or sequential administration of a compound of Formula (I), or compound 1, or compound 2, or compound 3 or compound 4, or a pharmaceutically acceptable salt thereof, optionally a proteasome inhibitor, or a pharmaceutically acceptable salt thereof, and one or more additional therapeutic agents, such that therapeutically effective amounts of a compound of Formula (I), or compound 1, or compound 2, or compound 3 or compound 4, or a pharmaceutically acceptable salt thereof, and optionally a proteasome inhibitor, or a pharmaceutically acceptable salt thereof, and the one or more additional therapeutic agents are both present in the body of the patient. When administered sequentially, the combination may be administered in two or more administrations.

Co-administration includes administration of unit dosages of a compound of Formula (I), or compound 1, or compound 2, or compound 3 or compound 4, or a pharmaceutically acceptable salt thereof, with or without a proteasome inhibitor, or a pharmaceutically acceptable salt thereof, before or after administration of unit dosages of one or more additional therapeutic agents. For example, a compound of Formula (I), or compound 1, or compound 2, or compound 3 or compound 4, or a pharmaceutically acceptable salt thereof, with or without a proteasome inhibitor, or a pharmaceutically acceptable salt thereof, may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound of Formula (I), or compound 1, or compound 2, or compound 3 or compound 4, or a pharmaceutically acceptable salt thereof, with or without a proteasome inhibitor, or a pharmaceutically acceptable salt thereof, within seconds or minutes. In other embodiments, a unit dose of a compound of Formula (I), or compound 1, or compound 2, or compound 3 or compound 4, or a pharmaceutically acceptable salt thereof, with or without a proteasome inhibitor, or a pharmaceutically acceptable salt thereof, is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound of Formula (I), or compound 1, or compound 2, or compound 3 or compound 4, or a pharmaceutically acceptable salt thereof, with or without a proteasome inhibitor, or a pharmaceutically acceptable salt thereof. If present, the proteasome inhibitor may be administered by any route (including orally or parenterally) before, at the same time, or later than the compound of Formula (I), or compound 1, or compound 2, or compound 3 or compound 4. If present, the proteasome inhibitor may be administered by any route (including orally or parenterally) before, at the same time, or later than the one or more additional therapeutic agents.

In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is combined with one or more additional therapeutic agents in a unitary dosage form for simultaneous administration to a patient, for example as a solid dosage form for oral administration.

In certain embodiments, such tablets are suitable for once daily dosing.

In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

HIV Combination Therapy

In the above embodiments, the additional therapeutic agent may be an anti-HIV agent. For example, in some embodiments, the additional therapeutic agent is selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide, emtricitabine, and rilpivirine; tenofovir alafenamide, emtricitabine, and bictegravir; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; tenofovir alafenamide hemifumarate, emtricitabine, and bictegravir; tenofovir alafenamide hemifumarate, emtricitabine, and bictegravir sodium; GENVOYA®; DESCOVY®; ODEFSEY®; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, H1viral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, BIT-225, CYT-107, HGTV-43, HS-10234, IMO-3100, IND-02, MK-1376, MK-8507, MK-8591, NOV-205, PA-1050040 (PA-040), PGC-007, SCY-635, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, and VM-1500.

Examples of HIV nucleoside or nucleotide inhibitors of reverse transcriptase include adefovir, adefovir dipivoxil, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, fozivudine tidoxil, lamivudine, phosphazid, stavudine, zalcitabine, zidovudine, and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, cabotegravir, and bictegravir.

Examples of HIV non-catalytic site, or allosteric, integrase inhibitors (NCINI) include CX-05045, CX-05168, T-169, and CX-14442.

HIV Entry Inhibitors

Examples of HIV entry (fusion) inhibitors include ceniicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), TD-0680, and vMIP (Haimipu).

Examples of gp41 inhibitors include albuvirtide, enfuvirtide, and sifuvirtide.

Examples of CD4 attachment inhibitors include ibalizumab.

Examples of gp120 inhibitors include Radha-108 (receptol) and BMS-663068

Examples of CXCR4 inhibitors include plerixafor, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, BET-bromodomain 4 (BRD4) inhibitors, ionomycin, PMA, SAHA (suberanilohydroxamic acid, or suberoyl, anilide, and hydroxamic acid), IL-15, JQ1, disulfram, amphotericin B, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, and HIV p24 capsid protein inhibitors.

Immune-based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; rintatolimod; IL-12; WF-10; VGV-1; MOR-22; BMS-936559; and IR-103.

Phosphatidylinositol 3-kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

HIV Antibodies, Bispecific Antibodies, and "Antibody-like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, BMS-936559, TMB-360, and those targeting HIV gp120 or gp41.

Examples of those targeting HIV gp120 or gp41 include bavituximab, UB-421, C2F5, C2G12, C4E10, C2F5+

C2G12+C4E10, 3-BNC-117, PGT145, PGT121, MDX010 (ipilimumab), VRC01, A32, 7B2, 10E8, VRC-07-523, and VRC07.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), and WO 2013/091096 (Boehringer Ingelheim).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/ AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-05, VAC-3S, multiclade DNA recombinant adenovirus-5 (rAd5), Pennvax-G, Pennvax-GP, VRC-HIV MAB060-00-AB, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140 [delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, and virus-like particle vaccines such as pseudovirion vaccine.

HIV Combination Therapy

In a particular embodiment, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); Hlviral; lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In a specific embodiment, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is administered or combined with an HIV nucleoside or nucleotide inhibitor of reverse transcriptase, and an HIV protease inhibiting compound. In an additional embodiment, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with an HIV nucleoside or nucleotide inhibitor of reverse transcriptase, an HIV non-nucleoside inhibitor of reverse transcriptase, and a pharmacokinetic enhancer. In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with at least one HIV nucleoside inhibitor of reverse transcriptase, an integrase inhibitor, and a pharmacokinetic enhancer. In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with at least one HIV nucleoside inhibitor of reverse transcriptase, and an integrase inhibitor. In another embodiment, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with two HIV nucleoside or nucleotide inhibitors of reverse transcriptase. In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with at least two HIV nucleoside or nucleotide inhibitors of reverse transcriptase, and an integrase inhibitor. In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with two HIV nucleoside or nucleotide inhibitors of reverse transcriptase, and an integrase inhibitor.

In a particular embodiment, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In a particular embodiment, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with tenofovir, tenofovir disoproxil, tenofovir disoproxil fumarate, tenofovir alafenamide, or tenofovir alafenamide hemifumarate.

In a particular embodiment, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

A compound of Formula (I), or compound 1, or compound 2, or compound 3 or compound 4, or a pharmaceutically acceptable salt thereof, with or without a proteasome inhibitor, or a pharmaceutically acceptable salt thereof, may be administered or combined with one or more additional therapeutic agents in any dosage amount of the compound of Formula (I), or compound 1, or compound 2, or compound 3 or compound 4, or a pharmaceutically acceptable salt thereof, (e.g., from 50 mg to 1000 mg of compound) and, if present, any dosage amount of the proteasome inhibitor (e.g., from 50 mg to 1000 mg of compound).

In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with 5-30 mg tenofovir alafenamide fumarate, tenofovir alafenamide hemifumarate, or tenofovir alafenamide, and 200 mg emtricitabine. In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with 10 mg tenofovir alafenamide fumarate, tenofovir alafenamide hemifumarate, or tenofovir alafenamide, and 200 mg emtricitabine. In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with 25 mg tenofovir alafenamide fumarate, tenofovir alafenamide hemifumarate, or tenofovir alafenamide, and 200 mg emtricitabine. A compound of Formula (I), or compound 1, or compound 2, or compound 3 or compound 4, or a pharmaceutically acceptable salt thereof, with or without a proteasome inhibitor, or a pharmaceutically acceptable salt thereof, may be administered or combined with the agents provided herein in any dosage amount of the compound (e.g., from 50 mg to 500 mg of compound) and, if present any dosage amount of proteasome inhibitor (e.g., from 50 mg to 500 mg of compound) the same as if each combination of dosages were specifically and individually listed.

In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with 200-400 mg tenofovir disoproxil fumarate, tenofovir disoproxil hemifumarate, or tenofovir disoproxil, and 200 mg emtricitabine. In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with 300 mg tenofovir disoproxil fumarate, tenofovir disoproxil hemifumarate, or tenofovir disoproxil, and 200 mg emtricitabine. A compound of Formula (I), or compound 1, or compound 2, or compound 3 or compound 4, or a pharmaceutically acceptable salt thereof, with or without a proteasome inhibitor, or a pharmaceutically acceptable salt thereof, may be administered or combined with the agents provided herein in any dosage amount of the compound (e.g., from 50 mg to 500 mg of compound) and, if present, any dosage amount of the proteasome inhibitor (e.g., from 50 mg to 500 mg of compound) the same as if each combination of dosages were specifically and individually listed.

In certain embodiments, a compound of Formula (I), or compound 1, or compound 2, or compound 3 or compound 4, or a pharmaceutically acceptable salt thereof, with or without a proteasome inhibitor, or a pharmaceutically acceptable salt thereof, is administered or combined with a cART (combination antiretroviral therapy) treatment. In some embodiments, the cART treatment is selected from the group consisting of tenofovir disoproxil/emtricitabine, tenofovir alafenamide/emtricitabine, tenofovir disoproxil/elvitegravir, tenofovir alafenamide/elvitegravir, tenofovir disoproxil/elvitegravir, tenofovir alafenamide/elvitegravir, tenofovir disoproxil/efavirenz, tenofovir alafenamide/efavirenz, tenofovir disoproxil/atazanavir, tenofovir alafenamide/atazanavir, tenofovir disoproxil/darunavir, tenofovir alafenamide/darunavir, tenofovir disoproxil/raltegravir, tenofovir alafenamide/raltegravir, tenofovir disoproxil/rilpivirine, tenofovir alafenamide/rilpivirine, tenofovir disoproxil/dolutegravir, tenofovir alafenamide/dolutegravir, emtricitabine/elvitegravir, emtricitabine/efavirenz, emtricitabine/atazanavir, emtricitabine/darunavir, emtricitabine/raltegravir, emtricitabine/rilpivirine, emtricitabine/dolutegravir, elvitegravir/efavirenz, elvitegravir/atazanavir, elvitegravir/darunavir, elvitegravir/raltegravir, elvitegravir/rilpivirine, efavirenz/atazanavir, efavirenz/darunavir, efavirenz/raltegravir, efavirenz/rilpivirine, atazanavir/darunavir, atazanavir/raltegravir, atazanavir/rilpivirine, darunavir/raltegravir, darunavir/rilpivirine, raltegravir/rilpivirine, darunavir/ritonavir, GSK1265744/rilpivirine, lamivudine/raltegravir, tenofovir disoproxil/emtricitabine/dolutegravir, tenofovir alafenamide/emtricitabine/dolutegravir, tenofovir disoproxil/emtricitabine/elvitegravir, tenofovir alafenamide/emtricitabine/elvitegravir, tenofovir disoproxil/emtricitabine/efavirenz, tenofovir alafenamide/emtricitabine/efavirenz, tenofovir disoproxil/emtricitabine/atazanavir, tenofovir alafenamide/emtricitabine/atazanavir, tenofovir disoproxil/emtricitabine/darunavir, tenofovir alafenamide/emtricitabine/darunavir, tenofovir disoproxil/emtricitabine/raltegravir, tenofovir alafenamide/emtricitabine/raltegravir, tenofovir disoproxil/emtricitabine/rilpivirine, tenofovir alafenamide/emtricitabine/rilpivirine, tenofovir disoproxil/elvitegravir/efavirenz, tenofovir alafenamide/elvitegravir/efavirenz, tenofovir disoproxil/elvitegravir/atazanavir, tenofovir alafenamide/elvitegravir/atazanavir, tenofovir disoproxil/elvitegravir/darunavir, tenofovir alafenamide/elvitegravir/darunavir, tenofovir disoproxil/elvitegravir/raltegravir, tenofovir alafenamide/elvitegravir/raltegravir, tenofovir disoproxil/elvitegravir/rilpivirine, tenofovir alafenamide/elvitegravir/rilpivirine, tenofovir disoproxil/efavirenz/atazanavir, tenofovir alafenamide/efavirenz/atazanavir, tenofovir disoproxil/efavirenz/darunavir, tenofovir alafenamide/efavirenz/darunavir, tenofovir disoproxil/efavirenz/raltegravir, tenofovir alafenamide/efavirenz/raltegravir, tenofovir disoproxil/efavirenz/rilpivirine tenofovir alafenamide/efavirenz/rilpivirine, tenofovir disoproxil/atazanavir/darunavir, tenofovir alafenamide/atazanavir/darunavir, tenofovir disoproxil/atazanavir/raltegravir, tenofovir alafenamide/atazanavir/raltegravir, tenofovir disoproxil/atazanavir/rilpivirine, tenofovir alafenamide/atazanavir/rilpivirine, tenofovir disoproxil/darunavir/raltegravir, tenofovir alafenamide/darunavir/raltegravir, tenofovir disoproxil/darunavir/rilpivirine, tenofovir alafenamide/darunavir/rilpivirine, tenofovir disoproxil/raltegravir/rilpivirine, tenofovir alafenamide/raltegravir/rilpivirine, emtricitabine/elvitegravir/efavirenz, emtricitabine/elvitegravir/atazanavir, emtricitabine/elvitegravir/darunavir, emtricitabine/elvitegravir/raltegravir, emtricitabine/elvitegravir/rilpivirine, emtricitabine/efavirenz/atazanavir, emtricitabine/efavirenz/darunavir, emtricitabine/efavirenz/raltegravir, emtricitabine/efavirenz/rilpivirine, emtricitabine/atazanavir/darunavir, emtricitabine/atazanavir/raltegravir, emtricitabine/atazanavir/rilpivirine, emtricitabine/darunavir/raltegravir, emtricitabine/darunavir/rilpivirine, emtricitabine/raltegravir/rilpivirine, elvitegravir/efavirenz/atazanavir, elvitegravir/efavirenz/darunavir, elvitegravir/efavirenz/raltegravir, elvitegravir/efavirenz/rilpivirine, elvitegravir/atazanavir/darunavir, elvitegravir/atazanavir/raltegravir, elvitegravir/atazanavir/rilpivirine, elvitegravir/darunavir/raltegravir, elvitegravir/darunavir/rilpivirine, elvitegravir/raltegravir/rilpivirine, efavirenz/atazanavir/darunavir, efavirenz/atazanavir/raltegravir, efavirenz/atazanavir/rilpivirine, efavirenz/darunavir/raltegravir, efavirenz/darunavir/rilpivirine, efavirenz/raltegravir/rilpivirine, atazanavir/darunavir/raltegravir, atazanavir/darunavir/rilpivirine, darunavir/raltegravir/rilpivirine, dolutegravir/abacavir/lamivudine, raltegravir/darunavir, raltegravir/ritonavir/darunavir, raltegravir/cobicistat/darunavir, raltegravir/atazanavir, raltegravir/atazanavir/maraviroc, raltegravir/maraviroc/etravirine, raltegravir/maraviroc/rilpivirine, maraviroc/darunavir/ritonavir, maraviroc/darunavir/cobicistat, raltegravir/darunavir/ritonavir/maraviroc, raltegravir/darunavir/cobicistat/maraviroc, raltegravir/darunavir/ritonavir/etravirine, raltegravir/darunavir/cobicistat/etravirine, atazanavir/ritonavir/efavirenz, atazanavir/cobicistat/efavirenz, raltegravir/etravirine, ritonavir/lopinavir/raltegravir, cobicistat/lopinavir/raltegravir, ritonavir/darunavir/etravirine, cobicistat/darunavir/etravirine, ritonavir/lopinavir and ritonavir/lopinavir/maraviroc, tenofovir disoproxil/bictegravir, tenofovir alafenamide/bictegravir, tenofovir disoproxil/emtricitabine/bictegravir, tenofovir alafenamide/emtricitabine/bictegravir, tenofovir alafenamide hemifumarate/emtricitabine/bictegravir sodium, tenofovir disoproxil/cabotegravir, tenofovir alafenamide/cabotegravir, tenofovir disoproxil/emtricitabine/cabotegravir, tenofovir alafenamide/emtricitabine/cabotegravir, cabotegravir/rilpivirine.

In one embodiment, kits comprising a compound of Formula (I), or compound 1, or compound 2, or compound 3 or compound 4, or a pharmaceutically acceptable salt thereof, with or without a proteasome inhibitor, or a pharmaceutically acceptable salt thereof, in combination with one or more (e.g., one, two, three, one or two, or one to three) additional therapeutic agents are provided.

In the following description of the examples, specific embodiments in which the invention may be practiced are described. These embodiments are described in sufficient detail to enable those skilled in the art to practice the invention. Other embodiments may be utilized and logical and other changes may be made without departing from the scope of the invention. The following detailed description is, therefore, not to be taken in a limiting sense, and the scope of the invention is defined only by the appended claims, along with the full scope of equivalents to which such claims are entitled.

EXAMPLES

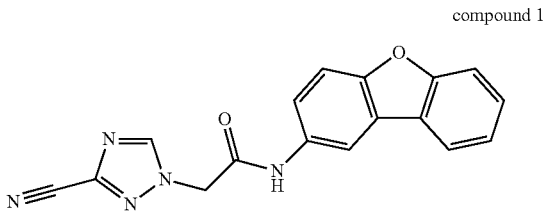

compound 1

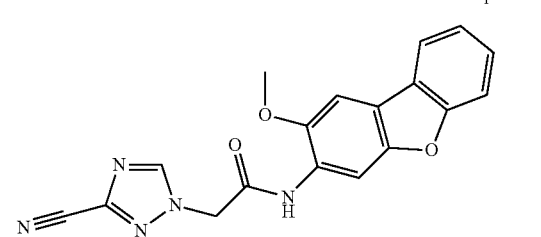

compound 2

Compound 1 and compound 2 were purchased from Enamine Ltd (Monmouth Jct., N.J.).

Example 1

Synthesis of 2-(3-cyano-1H-1,2,4-triazol-1-yl)-N-(2-(prop-2-yn-1-yloxy)dibenzo[b,d]furan-3-yl)acetamide (compound 4)

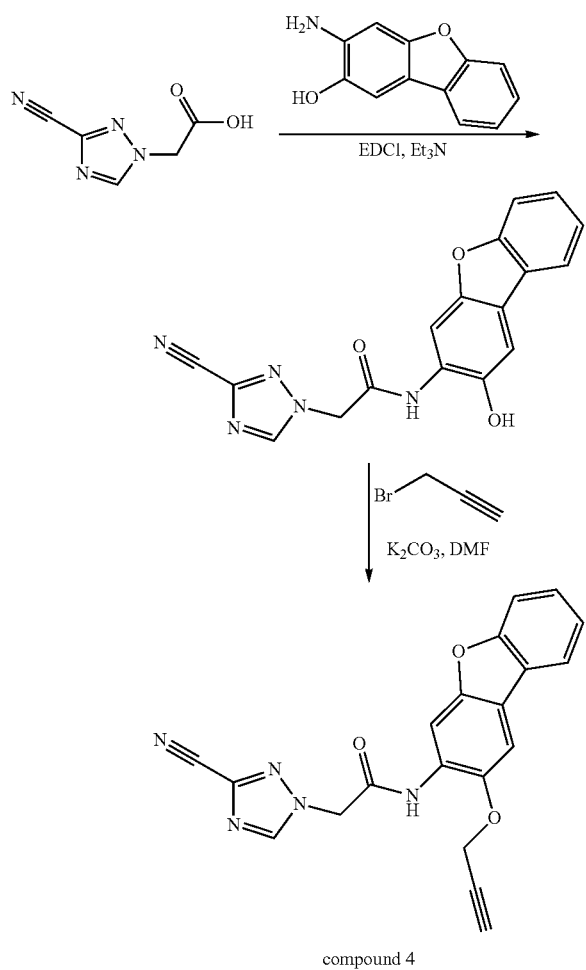

compound 4

2-(3-cyano-1H-1,2,4-triazol-1-yl)acetic acid (38 mg, 0.25 mmol) and 3-aminodibenzo[b,d]furan-2-ol (50 mg, 0.25 mmol) were dissolved in 3 mL dichloromethane. EDCI (1-Ethyl-3-(3-dimethylaminopropyl)carbodiimide, 72 mg, 0.38 mmol) was added followed by triethylamine (76 mg, 0.75 mmol). The mixture was stirred at ambient temperature for 5 hours, then diluted with 1N HCl (10 mL) and extracted with ethyl acetate. The organic phase was washed with brine and evaporated under vacuum. The crude product was purified by flash chromatography on 4 g silica gel with 0-100% ethyl acetate in hexane as eluent which gave 2-(3-cyano-1H-1,2,4-triazol-1-yl)-N-(2-hydroxydibenzo[b,d]furan-3-yl)acetamide.

2-(3-cyano-1H-1,2,4-triazol-1-yl)-N-(2-hydroxydibenzo[b,d]furan-3-yl)acetamide (25 mg, 0.075 mmol) was dissolved in DMF (3 mL). Anhydrous potassium carbonate (47 mg, 0.75 mmol) was added followed by 3-bromopropyne (0.04 mL, 0.38 mmol). The mixture was stirred at ambient temperature for 2 hours, then diluted with ethyl acetate, washed with water and brine, and evaporated under vacuum. The residue was purified by preparative HPLC followed by flash chromatography on 4 g silica gel with 10-80% ethyl acetate in hexane as eluent which gave 2-(3-cyano-1H-1,2,4-triazol-1-yl)-N-(2-(prop-2-yn-1-yloxy)dibenzo[b,d]furan-3-yl)acetamide. 1H NMR (400 MHz, DMSO-d6) δ 10.08 (s, 1H), 8.95 (s, 1H), 8.34 (s, 1H), 8.05 (d, J=7.4 Hz, 1H), 7.92 (s, 1H), 7.64 (d, J=8.2 Hz, 1H), 7.48-7.34 (m, 2H), 5.48 (s, 2H), 5.03 (s, 2H), 3.64 (s, 1H). MS (m/z) 372.3 [M+H]+.

Example 2

Synthesis of 2-(3-cyano-1H-1,2,4-triazol-1-yl)-N-(9-oxo-9H-fluoren-2-yl)acetamide (compound 3)

2-(3-cyano-1H-1,2,4-triazol-1-yl)-N-(9-oxo-9H-fluoren-2-yl)acetamide was synthesized in similar fashion to example 1 by coupling 2-(3-cyano-1H-1,2,4-triazol-1-yl) acetic acid with 2-amino-9H-fluoren-9-one. MS (m/z) 330.1 [M+H]+.

Example 3

Induced HIV-1 Expression in Resting CD4 Cell Cultures from HIV-1 Infected Subjects on cART To assess the ability to activate HIV-1 expression in latently infected resting CD4 cell cultures, leukapheresis samples were obtained from HIV-1 infected subjects on combined antiretroviral therapy (cART) and virally suppressed with plasma HIV RNA <50 copies/mL for ≥1 year. The leukapheresis product was diluted with PBS and layered over Ficoll for isolation of PBMCs. PBMCs were treated with red blood cell lysis buffer and rested overnight (10 million cells/ml) in tissue culture medium (RPMI 1640 supplemented with 10% FBS and Pen/Strep) before the isolation of resting (CD69-CD25-HLA-DR-) CD4 T cells according to the manufacturer's instructions (EasySep Human CD4 T cell Enrichment Kit modified to also deplete CD69+, CD25+, or HLA-DR+ cells). Resting CD4 T cells were cultured in four replicate wells per condition with the indicated compounds or with dimethyl sulfoxide (DMSO, vehicle control) for 6 days. To assess latency reversal that occurs in response to mitogenic activation of T cells, cells were incubated with 50 ng/ml phorbol 12-myristate 13-acetate (PMA) and 500 ng/ml ionomycin. Unless otherwise indicated, continuous exposure was used. Where pulses are indicated, at the end of the pulse, cells were spun three times at 500×g for 5 min, supernatant was decanted and replaced with an equal volume of fresh media. When in combination with another compound that was not pulsed, the compound with continuous exposure was added back at the indicated concentration. The cultures were maintained in the presence of antivirals (elvitegravir and efavirenz at 100 nM each) to prevent viral spread and amplification in order to measure the quantity of virions produced (latency reversal) by the indicated compounds. At the end of the incubation period, cell-free culture supernatants were harvested and HIV-1 RNA levels were quantified by the COBAS® AmpliPrep/COBAS® TaqMan HIV-1 Test, v2.0 (Roche). Romidepsin was used as a control. Romidepsin is a HDAC inhibitor with HIV latency reversal activity (PLoS pathogens (2015), 11(9), e1005142). The combination of a phorbol ester (PMA) and a calcium ionophore (ionomycin) was also used as a mitogenic control that has strong HIV latency reversal activity. As this combination induces global T cell proliferation and activation, systemic administration would likely induce significant toxicity. As such, PMA and ionomycin are useful strictly as a tool to monitor the amount of virus that can be produced in response to a strongly activating stimuli.

TABLE 1

Activation of HIV-1 Expression by compound 1 in resting CD4 T cells from HIV-1 Infected Subjects on cART

| | Subject ID (n = 10) | 6 μM Compound 1 | 3 μM Compound 1 | 1 μM Compound 1 | 40 nM Romidepsin, 4 h pulse | PMA + ionomycin |
|---|---|---|---|---|---|---|
| Fold HIV Activation[a] | 1 | 2.91 | 4.04 | 0.630 | 14.2 | 20.4 |
| | 2 | 5.86 | 8.91 | 1.66 | 3.09 | 34.2 |
| | 3 | 4.79 | 1.23 | 1.05 | 3.43 | 96.0 |
| | 4 | 8.46 | 0.801 | ND[b] | 0.77 | 283 |
| | 5 | 12.9 | 3.10 | ND | 1.58 | 50.3 |
| | 8 | 3.22 | 1.13 | ND | 2.35 | 46.6 |
| | 9 | 7.30 | 2.98 | ND | 4.15 | 42.6 |
| | 10 | 2.82 | 1.26 | ND | 2.51 | 13.9 |
| | 11 | 3.56 | 3.94 | ND | 5.60 | 28.3 |
| | 12 | 36.2 | 15.4 | 0.535 | 16.3 | 68.5 |
| | 13 | 29.6 | 10.3 | 1.01 | 5.26 | 1130 |
| | 14 | 1.54 | 1.63 | 1.00 | 1.62 | 16.6 |
| | 15 | 10.8 | 4.82 | 1.00 | 1.25 | 113 |
| | 18 | 3.36 | 0.994 | ND | 2.18 | 45.9 |
| | 20 | 2.27 | 0.869 | ND | 1.12 | 6.63 |
| | 21 | 6.21 | 7.04 | ND | 0.88 | 15.5 |
| | 25 | 23.3 | 6.52 | 2.21 | 23.1 | 49.6 |
| | Geometric Mean | 6.32 | 2.94 | 1.03 | 2.73 | 46.7 |

[a]Fold HIV activation is calculated as a ratio of the concentration of HIV RNA detected in cell culture supernatants from compound treated samples relative to DMSO treated samples.
[b]ND indicates that the value was not determined.

TABLE 2

Activation of HIV-1 Expression by compound 2 in resting CD4 T cells from HIV-1 Infected Subjects on cART

| | Subject ID (n = 8) | 6 μM Compound 2 | 3 μM Compound 2 | 1 μM Compound 2 | 40 nM Romidepsin, 4 h pulse | PMA + ionomycin |
|---|---|---|---|---|---|---|
| Fold HIV Activation[a] | 1 | 4.16 | 4.03 | 1.21 | 14.2 | 20.4 |
| | 2 | 2.47 | 3.22 | 1.03 | 3.09 | 34.2 |
| | 3 | 4.41 | 2.03 | 1.04 | 3.43 | 96.0 |
| | 4 | ND[b] | 3.42 | ND | 0.77 | 283 |
| | 5 | ND | 1.77 | ND | 1.58 | 50.3 |
| | 8 | ND | 1.00 | ND | 2.35 | 46.6 |
| | 9 | ND | 2.70 | ND | 4.15 | 42.6 |
| | 11 | ND | 7.69 | ND | 5.60 | 28.3 |
| | Geometric Mean | 3.56 | 2.76 | 1.09 | 3.16 | 52.0 |

[a]Fold HIV activation is calculated as a ratio of the concentration of HIV RNA detected in cell culture supernatants from compound treated samples relative to DMSO treated samples.
[b]ND indicates that the value was not determined.

TABLE 3

Activation of HIV-1 Expression by compound 3 in resting CD4 T cells from HIV-1 Infected Subjects on cART

| | Subject ID (n = 8) | 6 μM Compound 3 | 3 μM Compound 3 | 1 μM Compound 3 | 40 nM Romidepsin, 4 h pulse | PMA + ionomycin |
|---|---|---|---|---|---|---|
| Fold HIV Activation[a] | 1 | 2.14 | 1.59 | 1.14 | 14.2 | 20.4 |
| | 2 | 2.21 | 2.54 | ND[b] | 3.09 | 34.2 |
| | 3 | 3.75 | 2.88 | 2.32 | 3.43 | 96.0 |
| | 4 | ND | 1.23 | ND | 0.77 | 283 |
| | 5 | ND | 3.24 | ND | 1.58 | 50.3 |
| | 8 | ND | 1.77 | ND | 2.35 | 46.6 |
| | 9 | ND | 2.42 | ND | 4.15 | 42.6 |
| | 11 | ND | 4.05 | ND | 5.60 | 28.3 |
| | Geometric Mean | 2.61 | 2.31 | 1.62 | 3.16 | 52.0 |

[a]Fold HIV activation is calculated as a ratio of the concentration of HIV RNA detected in cell culture supernatants from compound treated samples relative to DMSO treated samples.
[b]ND indicates that the value was not determined.

TABLE 4

Activation of HIV-1 Expression by compound 4 in resting CD4 T cells from HIV-1 Infected Subjects on cART

| | Subject ID (n = 5) | 6 µM Compound 4 | 3 µM Compound 4 | 1 µM Compound 4 | 40 nM Romidepsin, 4 h pulse | PMA + ionomycin |
|---|---|---|---|---|---|---|
| Fold HIV Activation[a] | 18 | 3.96 | 2.93 | ND[b] | 2.18 | 45.92 |
| | 19 | 4.53 | 1.69 | ND | 1.38 | 82.5 |
| | 20 | 3.03 | ND | ND | 1.12 | 6.63 |
| | 21 | 4.55 | ND | ND | 0.88 | 15.5 |
| | 25 | ND | 8.97 | 1.09 | 23.1 | 49.6 |
| | Geometric Mean | 3.97 | 3.54 | 1.09 | 2.33 | 28.7 |

[a]Fold HIV activation is calculated as a ratio of the concentration of HIV RNA detected in cell culture supernatants from compound treated samples relative to DMSO treated samples.
[b]ND indicates that the value was not determined.

TABLE 5

Synergistic activation of HIV-1 Expression by compound 1 and bortezomib in resting CD4 T cells from HIV-1 Infected Subjects on cART

| | Subject ID (n = 10) | 3 µM Compound 1 | 15 nM Bortezomib 24 h pulse | 15 nM Bortezomib 24 h pulse + 3 µM Compound 1 | PMA + Ionomycin |
|---|---|---|---|---|---|
| Fold HIV Activation[a] | 26 | 1.09 | 1.10 | 49.1 | 138.6 |
| | 4 | 0.80 | 3.47 | 232 | 283 |
| | 5 | 3.10 | 3.82 | 171 | 50.3 |
| | 12 | 15.4 | 0.77 | 39.6 | 68.5 |
| | 14 | 1.63 | 1.99 | 12.9 | 16.6 |
| | 15 | 4.82 | 0.88 | 13.6 | 113 |
| | 16 | 30.4 | 1.09 | 231 | 185 |
| | 23 | 0.97 | 0.39 | 3.04 | 11.5 |
| | 24 | 1.40 | 1.41 | 8.55 | 39.21 |
| | 25 | 6.52 | 1.84 | 144 | 49.6 |
| | Geometric Mean | 3.12 | 1.36 | 40.4 | 63.3 |

[a]Fold HIV activation is calculated as a ratio of the concentration of HIV RNA detected in cell culture supernatants from compound treated samples relative to DMSO treated samples.

TABLE 6

Synergistic activation of HIV-1 Expression by compound 1 and carfilzomib in resting CD4 T cells from HIV-1 Infected Subjects on cART

| | Subject ID (n = 9) | 3 µM Compound 1 | 0.3 µM Carfilzomib, 15 min pulse | 0.3 µM Carfilzomib, 15 min pulse + 3 µM Compound 1 | PMA + Ionomycin |
|---|---|---|---|---|---|
| Fold HIV Activation[a] | 6 | 1.86 | 2.97 | 50.1 | 32.2 |
| | 7 | 11.4 | 0.63 | 39.1 | 55.8 |
| | 8 | 1.13 | 0.91 | 8.59 | 46.6 |
| | 9 | 2.98 | 0.64 | 80.1 | 42.6 |
| | 10 | 1.26 | 1.00 | 0.69 | 13.9 |
| | 11 | 3.94 | 1.44 | 5.16 | 28.3 |
| | 14 | 1.63 | 0.89 | 7.08 | 16.6 |
| | 15 | 4.82 | 1.00 | 38.1 | 113 |
| | 16 | 30.4 | 1.05 | 248 | 185 |
| | Geometric Mean | 3.53 | 1.04 | 19.0 | 42.8 |

[a]Fold HIV activation is calculated as a ratio of the concentration of HIV RNA detected in cell culture supernatants from compound treated samples relative to DMSO treated samples.

TABLE 7

Synergistic activation of HIV-1 Expression by compound 1 and oprozomib in resting CD4 T cells from HIV-1 Infected Subjects on cART

| | Subject ID (n = 7) | 3 µM Compound 1 | 100 nM Oprozomib, 1 hr pulse | 100 nM Oprozomib, 1 hr pulse + 3 µM Compound 1 | PMA + Ionomycin |
|---|---|---|---|---|---|
| Fold HIV Activation[a] | 4 | 0.80 | 2.33 | 79.2 | 283 |
| | 5 | 3.10 | 1.59 | 251 | 50.3 |
| | 6 | 1.86 | 1.01 | 1.68 | 32.2 |
| | 7 | 11.4 | 6.67 | 34.3 | 55.8 |
| | 12 | 15.4 | 1.59 | 19.3 | 68.5 |
| | 13 | 10.3 | 3.56 | 240 | 1130 |
| | 16 | 30.4 | 3.02 | 320 | 185 |
| | Geometric Mean | 5.92 | 2.37 | 55.8 | 120 |

[a]Fold HIV activation is calculated as a ratio of the concentration of HIV RNA detected in cell culture supernatants from compound treated samples relative to DMSO treated samples.

TABLE 8

Synergistic activation of HIV-1 Expression by compound 2 and bortezomib in resting CD4 T cells from HIV-1 Infected Subjects on cART

| | Subject ID (n = 2) | 3 µM Compound 2 | 15 nM bortezomib, 24 hr pulse | 3 uM Compound 2 + 15 nM bortezomib, 24 hr pulse | PMA + Ionomycin |
|---|---|---|---|---|---|
| Fold HIV Activation[a] | 4 | 3.42 | 3.47 | 82.7 | 283 |
| | 5 | 1.77 | 3.82 | 166 | 50.3 |
| | Geometric Mean | 2.46 | 3.64 | 117 | 119 |

[a]Fold HIV activation is calculated as a ratio of the concentration of HIV RNA detected in cell culture supernatants from compound treated samples relative to DMSO treated samples.

TABLE 9

Synergistic activation of HIV-1 Expression by compound 3 and bortezomib in resting CD4 T cells from HIV-1 Infected Subjects on cART

| | Subject ID (n = 2) | 3 μM Compound 3 | 15 nM bortezomib, 24 hr pulse | 3 uM Compound 3 + 15 nM bortezomib, 24 hr pulse | PMA + Ionomycin |
|---|---|---|---|---|---|
| Fold HIV Activation[a] | 4 | 1.23 | 3.47 | 10.2 | 283 |
| | 5 | 3.24 | 3.82 | 69.0 | 50.3 |
| | Geometric Mean | 1.99 | 3.64 | 26.6 | 119 |

[a]Fold HIV activation is calculated as a ratio of the concentration of HIV RNA detected in cell culture supernatants from compound treated samples relative to DMSO treated samples.

TABLE 10

Synergistic activation of HIV-1 Expression by compound 4 and bortezomib in resting CD4 T cells from HIV-1 Infected Subjects on cART

| | Subject ID (n = 3) | 3 μM Compound 4 | 15 nM bortezomib, 24 hr pulse | 3 μM Compound 4 + 15 nM bortezomib, 24 hr pulse | PMA + Ionomycin |
|---|---|---|---|---|---|
| Fold HIV Activation[a] | 18 | 2.93 | 1.59 | 9.53 | 6.63 |
| | 19 | 1.69 | 3.81 | 102 | 45.9 |
| | 25 | 8.97 | 1.84 | 10.8 | 49.6 |
| | Geometric Mean | 3.54 | 2.23 | 21.9 | 24.7 |

[a]Fold HIV activation is calculated as a ratio of the concentration of HIV RNA detected in cell culture supernatants from compound treated samples relative to DMSO treated samples.

TABLE 11

Synergistic activation of HIV-1 Expression by compound 2 and carfilzomib in resting CD4 T cells from HIV-1 Infected Subjects on cART

| | Subject ID (n = 3) | 3 μM Compound 2 | 0.3 μM Carfilzomib, 15 min pulse | 3 μM Compound 2 + 0.3 μM Carfilzomib, 15 min pulse | PMA + Ionomycin |
|---|---|---|---|---|---|
| Fold HIV Activation[a] | 8 | 1.00 | 0.91 | 50.0 | 46.6 |
| | 9 | 2.70 | 0.64 | 97.7 | 42.6 |
| | 11 | 7.69 | 1.44 | 1.48 | 28.3 |
| | Geometric Mean | 2.75 | 0.94 | 19.3 | 38.3 |

[a]Fold HIV activation is calculated as a ratio of the concentration of HIV RNA detected in cell culture supernatants from compound treated samples relative to DMSO treated samples.

TABLE 12

Synergistic activation of HIV-1 Expression by compound 3 and carfilzomib in resting CD4 T cells from HIV-1 Infected Subjects on cART

| | Subject ID (n = 3) | 3 μM Compound 3 | 0.3 μM Carfilzomib, 15 min pulse | 3 μM Compound 3 + 0.3 μM Carfilzomib, 15 min pulse | PMA + Ionomycin |
|---|---|---|---|---|---|
| Fold HIV Activation[a] | 8 | 1.77 | 0.91 | 3.59 | 46.6 |
| | 9 | 2.42 | 0.64 | 10.4 | 42.6 |
| | 11 | 4.05 | 1.44 | 1.26 | 28.3 |
| | Geometric Mean | 2.59 | 0.94 | 3.61 | 38.3 |

[a]Fold HIV activation is calculated as a ratio of the concentration of HIV RNA detected in cell culture supernatants from compound treated samples relative to DMSO treated samples.

The invention claimed is:

1. A compound of Formula (I)

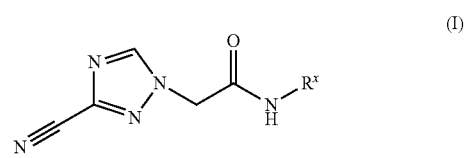

or a pharmaceutically acceptable salt thereof, wherein:
$R^x$ is selected from the group consisting of

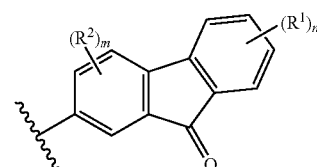

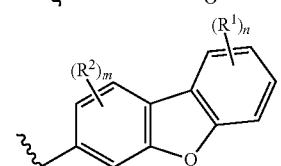

and

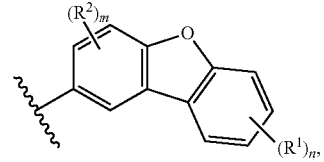

each $R^2$ is independently selected from the group consisting of halogen, $C_{1-6}$alkyl, $C_{2-6}$alkynyl, $C_{2-6}$alkenyl, $C_{1-6}$haloalkyl, $C_{1-6}$heteroalkyl, CN, $NR^aR^b$, $SR^a$ and $OR^a$, each $R^1$ is independently selected from the group consisting of halogen, $C_{1-6}$alkyl, $C_{1-6}$haloalkyl, $C_{1-6}$heteroalkyl, CN, $NH_2$, $NR^cR^d$, $SR^c$, and $OR^c$, each $R^a$ is independently selected from the group consisting of H, $C_{1-6}$alkyl, $C_{1-6}$haloalkyl, $C_{2-6}$alkynyl, and $C_{2-6}$alkenyl, each $R^b$ is independently selected from the group consisting of H, $C_{1-6}$alkyl, $C_{1-6}$haloalkyl, $C_{2-6}$alkynyl, and $C_{2-6}$alkenyl, each $R^c$ is independently selected from the group consisting of $C_{1-6}$alkyl, and $C_{1-6}$haloalkyl, each $R^d$ is independently selected from the group consisting of H, $C_{1-6}$alkyl, and $C_{1-6}$haloalkyl,
n is 0, 1, 2, 3, or 4, and
m is 0, 1, 2, or 3,
provided that the compound is not

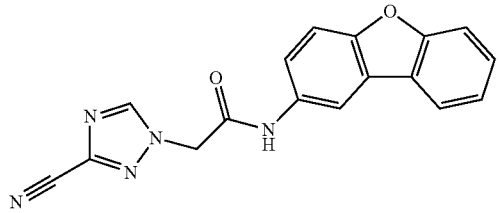

or

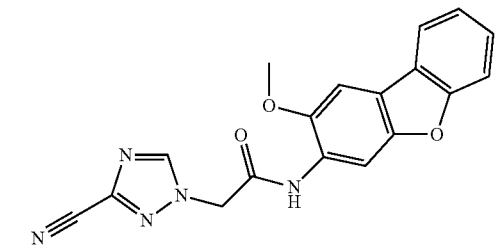

.

2. The compound of claim 1, wherein m=0.
3. The compound of claim 1, wherein m=1 and $R^2$ is —$OR^a$.
4. The compound of claim 3, wherein $R^a$ is independently selected from the group consisting of $C_{1-6}$alkyl, and $C_{2-6}$alkynyl.
5. The compound of claim 4, wherein $R^a$ is methyl or —$CH_2C\equiv CH$.
6. The compound of claim 5, wherein n=0.
7. The compound of claim 1 selected from the group consisting of:

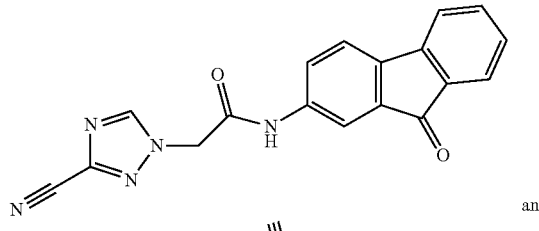

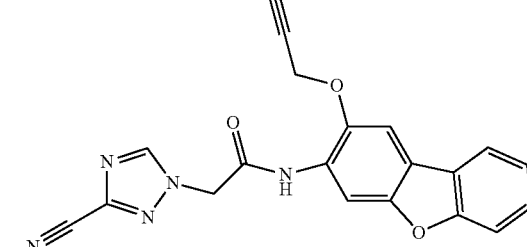

or a pharmaceutically acceptable salt thereof.
8. A pharmaceutically acceptable composition comprising a compound of claim 1 or a pharmaceutically acceptable salt thereof.
9. The composition of claim 8, further comprising one or more pharmaceutically acceptable excipients.
10. The composition of claim 9, further comprising one or more anti-HIV agents.

11. A pharmaceutically acceptable composition comprising a compound of claim 1 or a compound of Formula:

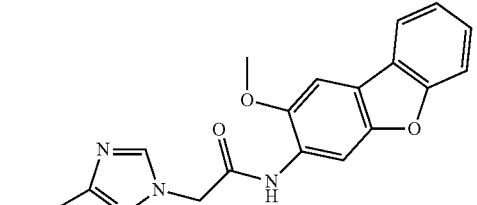

or

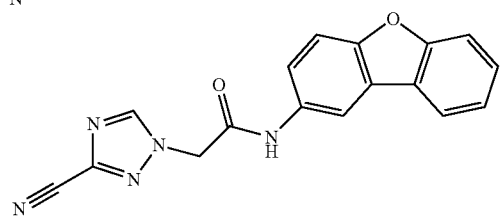

or a pharmaceutically acceptable salt thereof, and a proteasome inhibitor, or a pharmaceutically acceptable salt thereof.

12. The composition of claim 11, wherein the compound is selected from the group consisting of:

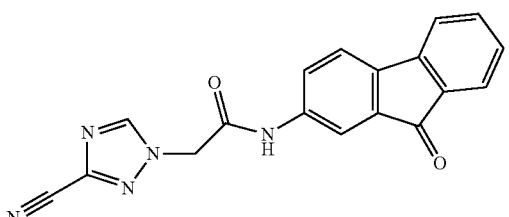

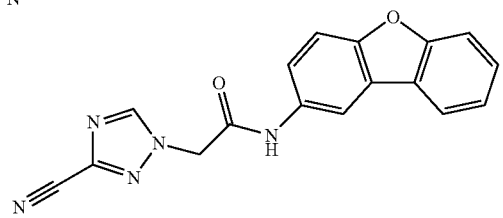

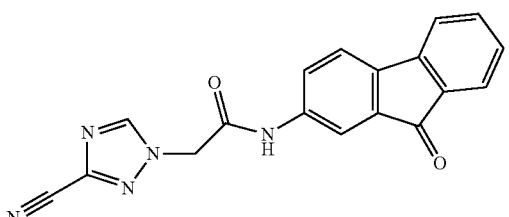

and

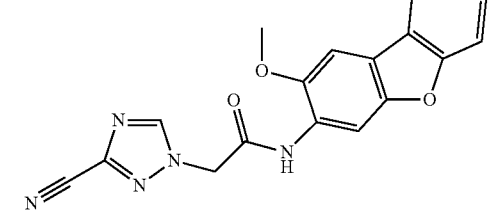

or a pharmaceutically acceptable salt thereof.

13. The composition of claim 11, wherein the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

14. The composition of claim 11, wherein the proteasome inhibitor is selected from the group consisting of bortezomib, carfilzomib, and oprozomib, or a pharmaceutically acceptable salt thereof.

15. The composition of claim 11, further comprising one or more pharmaceutically acceptable excipients.

16. The composition of claim 11, further comprising one or more anti-HIV agents.

17. A kit comprising:
   (1) a composition comprising a pharmaceutically effective amount of a compound of claim 1 or a compound of Formula:

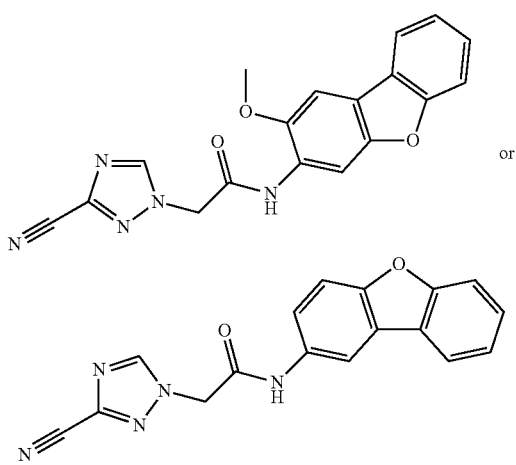

or a pharmaceutically acceptable salt thereof;
   (2) a composition comprising a pharmaceutically effective amount of a proteasome inhibitor, or a pharmaceutically acceptable salt thereof; and
   (3) instructions for their co-administration.

18. The kit of claim 17, wherein the compound is selected from the group consisting of:

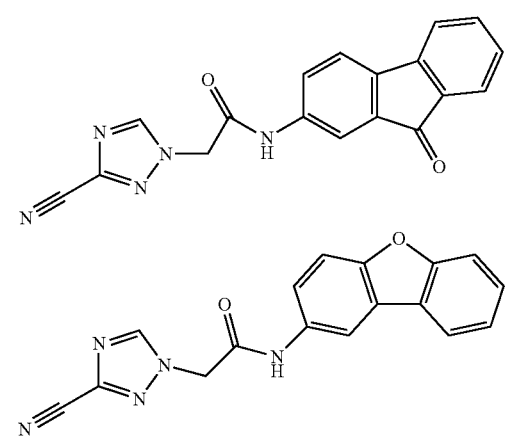

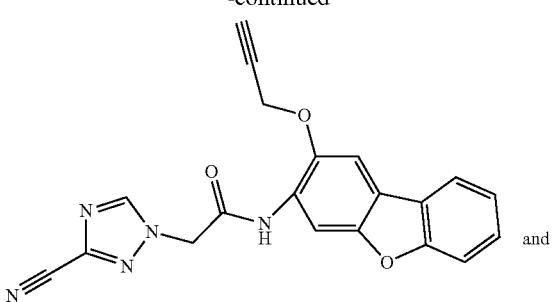

and

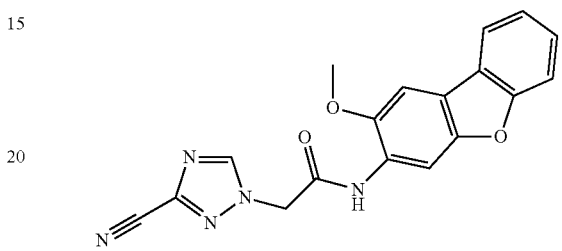

or a pharmaceutically acceptable salt thereof.

19. The kit of claim 17, wherein the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

20. The kit of claim 17, wherein the proteasome inhibitor is selected from the group consisting of bortezomib, carfilzomib, and oprozomib, or a pharmaceutically acceptable salt thereof.

21. A method of treating an HIV infection in a human, the method comprising administering to a human in need thereof a pharmaceutically effective amount of a compound of claim 1 or a compound of Formula:

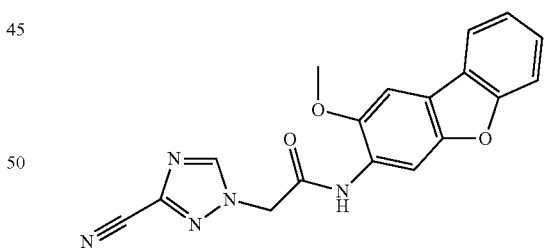

or

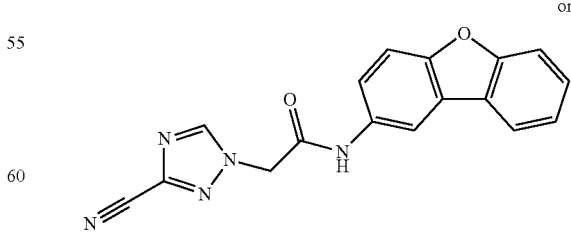

or a pharmaceutically acceptable salt thereof.

22. The method of claim 21 wherein the compound is selected from the group consisting of:

or a pharmaceutically acceptable salt thereof.

23. The method of claim 21, further comprising administering one or more anti-HIV agents.

24. A method of inducing HIV gene expression in a human infected with HIV, the method comprising administering to the human infected with HIV a pharmaceutically effective amount of a compound of claim 1 or a compound of Formula:

or a pharmaceutically acceptable salt thereof.

25. The method of claim 24, wherein the compound is selected from the group consisting of:

or a pharmaceutically acceptable salt thereof.

26. The method of claim 24, further comprising administering one or more anti-HIV agents.

27. A method of reducing the latent HIV reservoir in a human infected with HIV, the method comprising administering to the human a pharmaceutically effective amount of a compound of claim 1 or a compound of Formula:

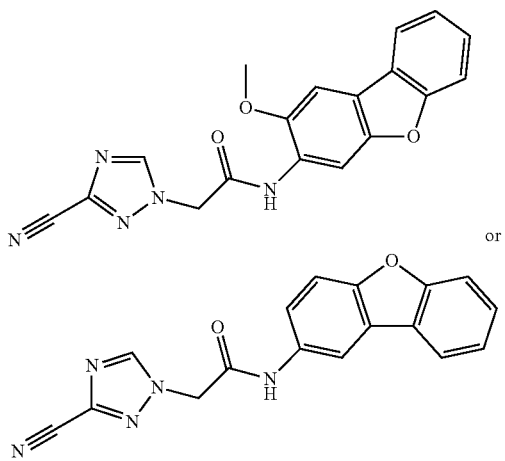

or a pharmaceutically acceptable salt thereof.

28. The method of claim 27, wherein the compound is selected from the group consisting of:

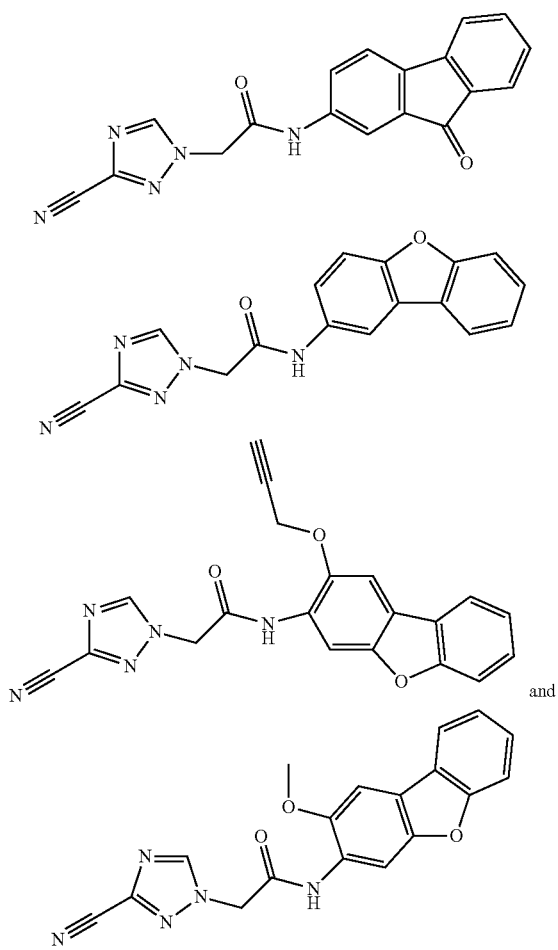

or a pharmaceutically acceptable salt thereof.

29. The method of claim 27, further comprising administering one or more anti-HIV agents.

30. A method of treating an HIV infection in a human, the method comprising administering to a human in need thereof a pharmaceutically effective amount of a compound of claim 1 or a compound of Formula:

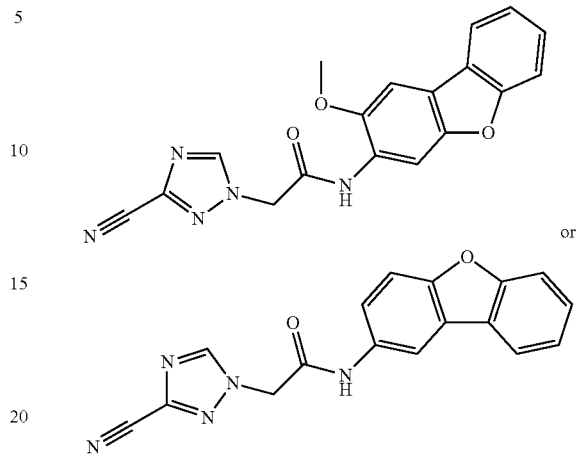

or a pharmaceutically acceptable salt thereof, and a pharmaceutically effective amount of a proteasome inhibitor, or a pharmaceutically acceptable salt thereof.

31. The method of claim 30, wherein the compound is selected from the group consisting of:

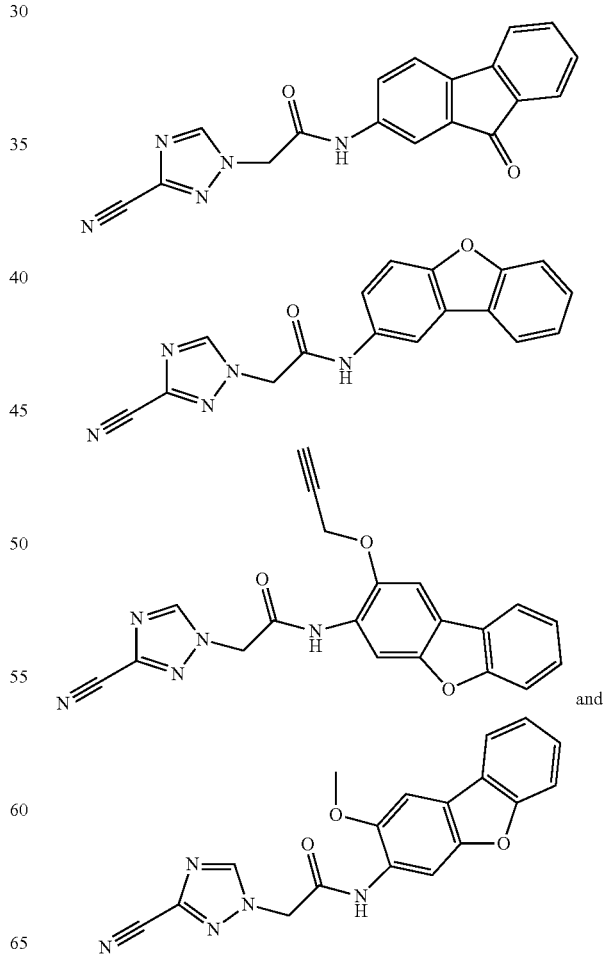

or a pharmaceutically acceptable salt thereof.

32. The method of claim 30, wherein the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

33. The method of claim 30, wherein the proteasome inhibitor is selected from the group consisting of bortezomib, carfilzomib, and oprozomib, or a pharmaceutically acceptable salt thereof.

34. A method of inducing HIV gene expression in a human infected with HIV, the method comprising administering to the human infected with HIV a pharmaceutically effective amount of a compound of claim 1 or a compound of Formula:

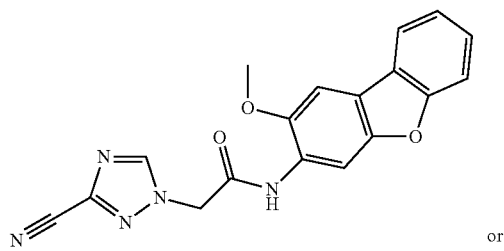

or

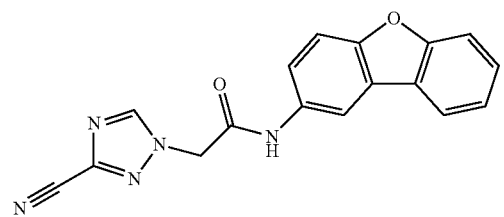

or a pharmaceutically acceptable salt thereof, and a pharmaceutically effective amount of a proteasome inhibitor, or a pharmaceutically acceptable salt thereof.

35. The method of claim 34, wherein the compound is selected from the group consisting of:

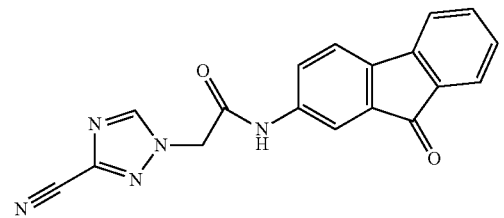

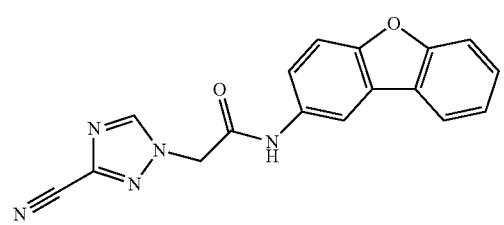

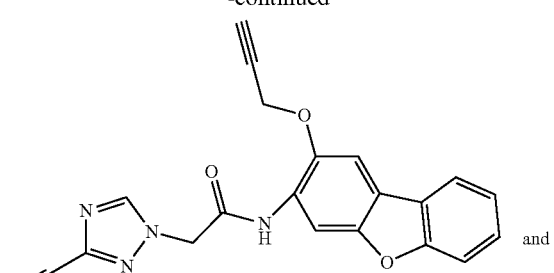

and

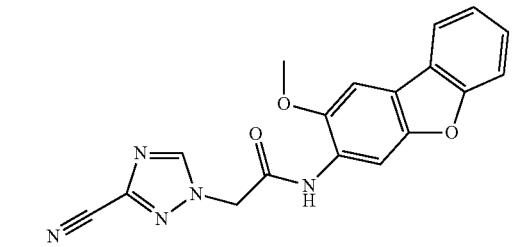

or a pharmaceutically acceptable salt thereof.

36. The method of claim 34, wherein the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

37. The method of claim 34, wherein the proteasome inhibitor is selected from the group consisting of bortezomib, carfilzomib, and oprozomib, or a pharmaceutically acceptable salt thereof.

38. A method of reducing the latent HIV reservoir in a human infected with HIV, the method comprising administering to the human a pharmaceutically effective amount of a compound of claim 1 or a compound of Formula:

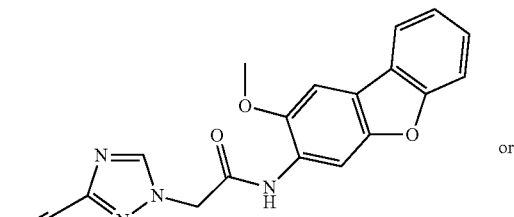

or

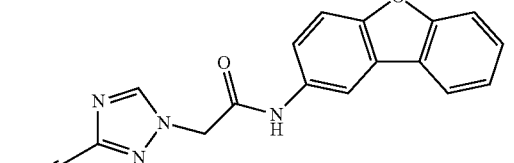

or a pharmaceutically acceptable salt thereof, and a pharmaceutically effective amount of a proteasome inhibitor, or a pharmaceutically acceptable salt thereof.

39. The method of claim 38, wherein the compound is selected from the group consisting of:

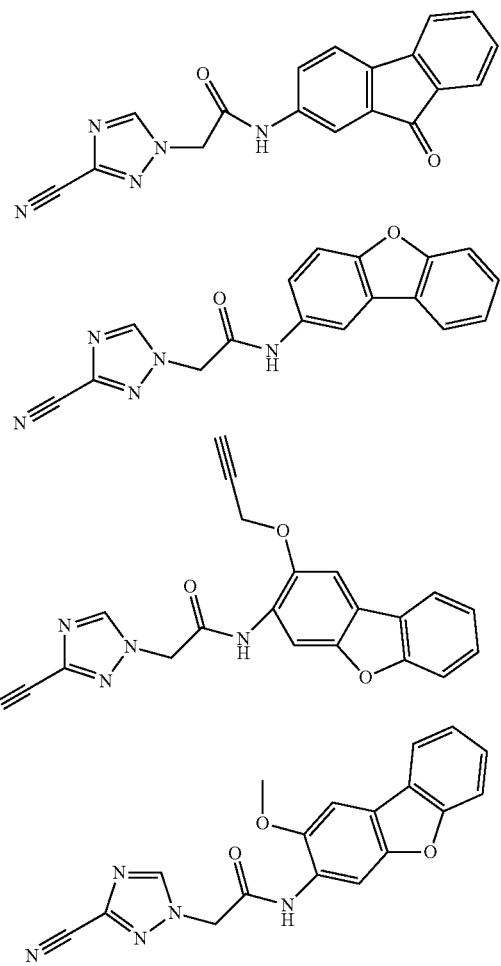

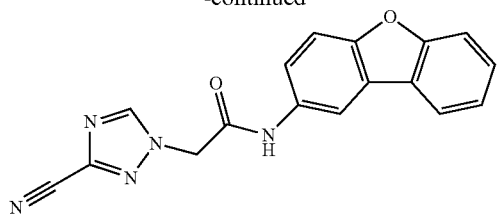

or a pharmaceutically acceptable salt thereof, and a pharmaceutically effective amount of a proteasome inhibitor, or a pharmaceutically acceptable salt thereof.

43. The method of claim 42, wherein the compound is selected from the group consisting of:

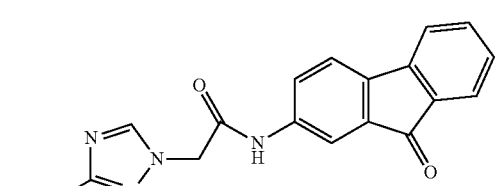

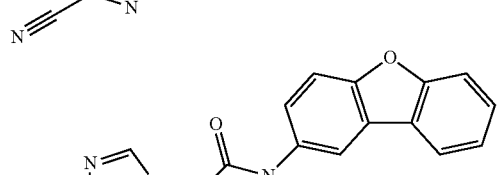

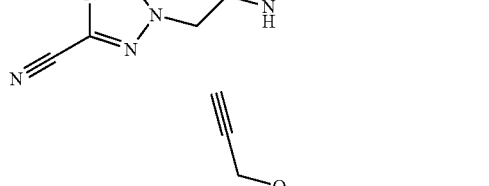

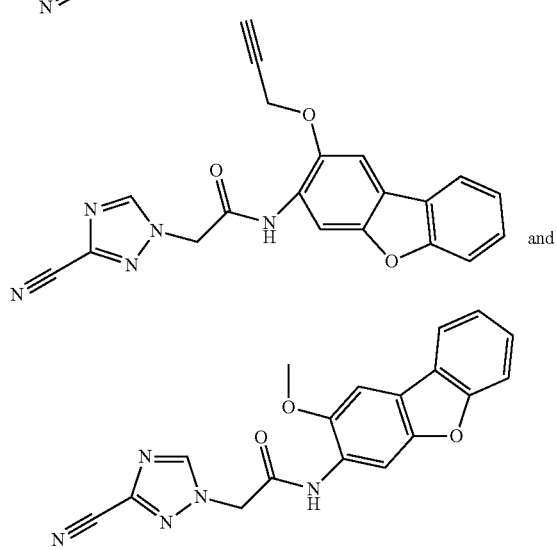

or a pharmaceutically acceptable salt thereof.

40. The method of claim 38, wherein the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

41. The method of claim 38, wherein the proteasome inhibitor is selected from the group consisting of bortezomib, carfilzomib, and oprozomib, or a pharmaceutically acceptable salt thereof.

42. A method of reducing HIV viremia in a human infected with HIV, the method comprising administering to the human a pharmaceutically effective amount of a compound of claim 1 or a compound of Formula:

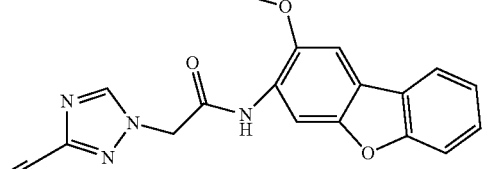

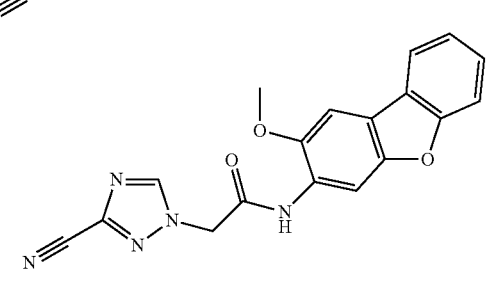

or a pharmaceutically acceptable salt thereof.

44. The method of claim 42, wherein the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

45. The method of claim 42, wherein the proteasome inhibitor is selected from the group consisting of bortezomib, carfilzomib, and oprozomib, or a pharmaceutically acceptable salt thereof.

46. A method of treating an HIV infection in a human, the method comprising:

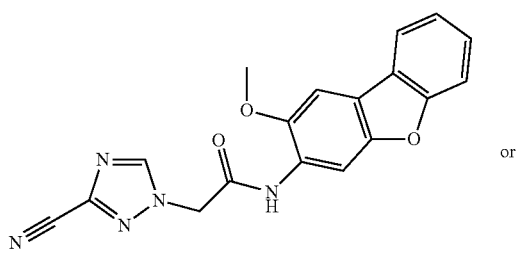

or a) administering to the human in need thereof a pharmaceutically effective amount of a combination antiretroviral therapy regimen sufficient to lower the level of HIV detected in the human's blood or plasma from a first level to a second level, the second level comprising a lower concentration of HIV in the human's blood or plasma than the concentration of HIV in the human's blood or plasma in the first level; and b) administering to the human a pharmaceutically effective amount of a compound of claim 1 or a compound of Formula:

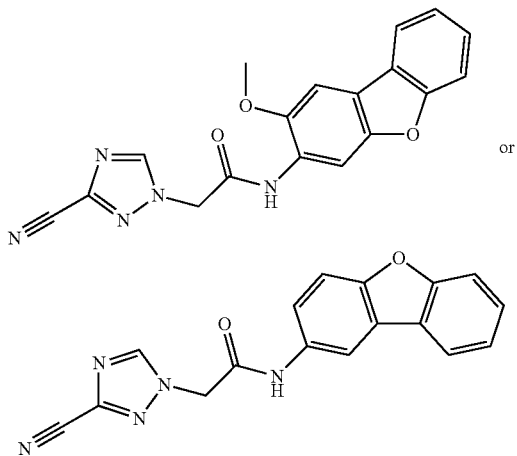

or

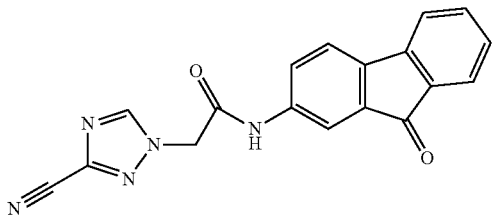

or a pharmaceutically acceptable salt thereof, and a pharmaceutically effective amount of a proteasome inhibitor, or a pharmaceutically acceptable salt thereof.

47. The method of claim 46, wherein the compound is selected from the group consisting of

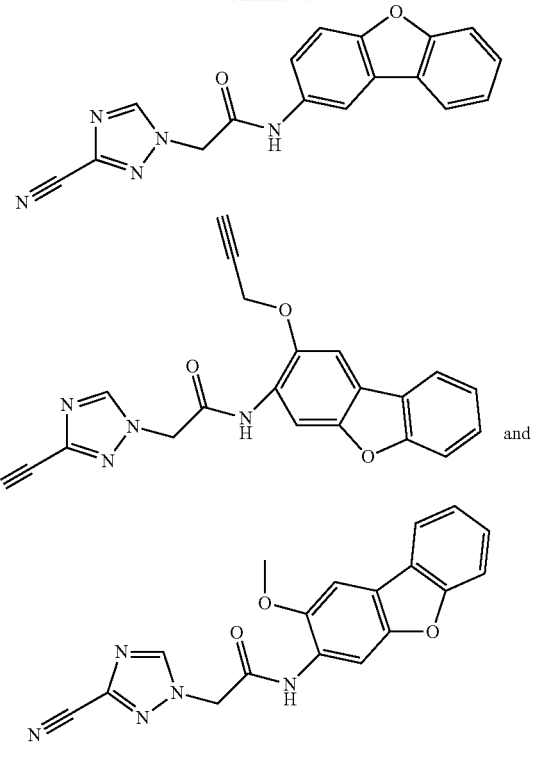

or a pharmaceutically acceptable salt thereof.

48. The method of claim 46, wherein the proteasome inhibitor is selected from the group consisting of bortezomib, carfilzomib, ixazomib, oprozomib, marizomib, VLX-1570, FV-214, FV-162, ONYX-0914, G4-1, LC-530110, VL-01, argyrin F, VR-23, and UK-202, or a pharmaceutically acceptable salt thereof.

49. The method of claim 46, wherein the proteasome inhibitor is selected from the group consisting of bortezomib, carfilzomib, and oprozomib, or a pharmaceutically acceptable salt thereof.

50. The method of claim 46, wherein step a) and step b) are conducted sequentially.

51. The method of claim 46, wherein step a) and step b) are conducted simultaneously.

* * * * *